(12) United States Patent
Kaib et al.

(10) Patent No.: US 10,376,169 B2
(45) Date of Patent: Aug. 13, 2019

(54) SYSTEMS AND METHODS OF DETERMINING LOCATION USING A MEDICAL DEVICE

(71) Applicant: ZOLL MEDICAL CORPORATION, Chelmsford, MA (US)

(72) Inventors: Thomas E. Kaib, Irwin, PA (US); Guy Johnson, Gloucester, MA (US)

(73) Assignee: ZOLL MEDICAL CORPORATION, Chelmsford, MA (US)

( * ) Notice: Subject to any disclaimer, the term of this patent is extended or adjusted under 35 U.S.C. 154(b) by 301 days.

(21) Appl. No.: 15/077,995

(22) Filed: Mar. 23, 2016

(65) Prior Publication Data
US 2016/0278652 A1    Sep. 29, 2016

Related U.S. Application Data

(60) Provisional application No. 62/137,470, filed on Mar. 24, 2015.

(51) Int. Cl.
*A61B 5/00* (2006.01)
*A61N 1/04* (2006.01)
(Continued)

(52) U.S. Cl.
CPC ............ *A61B 5/0408* (2013.01); *A61B 5/112* (2013.01); *A61B 5/1112* (2013.01);
(Continued)

(58) Field of Classification Search
CPC .... A61B 5/0408; A61B 5/1112–5/1113; A61B 5/6804; A61B 5/742; H04W 4/029;
(Continued)

(56) References Cited

U.S. PATENT DOCUMENTS

| 4,102,332 A | 7/1978 | Gessman |
| 5,544,661 A | 8/1996 | Davis et al. |

(Continued)

FOREIGN PATENT DOCUMENTS

| WO | 2002054945 A1 | 7/2002 |

OTHER PUBLICATIONS

Sebastian, Anthony. "Think GPS Is Cool? IPS Will Blow Your Mind." Web. Apr. 24, 2012. <http://www.extremetech.com/extreme/126843-think-gps-is-cool-ips-will-blow-your-mind>.
(Continued)

*Primary Examiner* — Paula J Stice
(74) *Attorney, Agent, or Firm* — Lando & Anastasi, LLP

(57) ABSTRACT

According to at least one aspect, a wearable medical device is provided. The wearable medical device may include a sensing electrode to sense an electrocardiogram signal of a patient, a therapy electrode to provide treatment to the patient, a garment to be worn about a torso of the patient and receive the sensing electrode and the therapy electrode, and a controller operatively coupled to the sensing electrode and the therapy electrode. The controller may be configured to determine a current location of the wearable medical device based on a previous position of the medical device and at least a speed and a direction of movement of the wearable medical device.

36 Claims, 11 Drawing Sheets

(51) Int. Cl.
| | |
|---|---|
| *A61B 5/0408* | (2006.01) |
| *H04W 4/029* | (2018.01) |
| *H04W 4/38* | (2018.01) |
| *A61B 5/11* | (2006.01) |
| *A61N 1/39* | (2006.01) |
| *H04W 4/04* | (2009.01) |
| *G16H 10/20* | (2018.01) |
| *G16H 80/00* | (2018.01) |
| *G16H 40/63* | (2018.01) |
| *G16H 40/67* | (2018.01) |
| *G16H 50/20* | (2018.01) |
| *G16H 20/30* | (2018.01) |
| *A61B 5/0205* | (2006.01) |

(52) U.S. Cl.
CPC .......... *A61B 5/1113* (2013.01); *A61B 5/6804* (2013.01); *A61B 5/742* (2013.01); *A61N 1/046* (2013.01); *A61N 1/0484* (2013.01); *A61N 1/3925* (2013.01); *G16H 10/20* (2018.01); *G16H 20/30* (2018.01); *G16H 40/63* (2018.01); *G16H 40/67* (2018.01); *G16H 50/20* (2018.01); *G16H 80/00* (2018.01); *H04W 4/029* (2018.02); *H04W 4/043* (2013.01); *H04W 4/38* (2018.02); *A61B 5/0205* (2013.01); *A61B 5/1118* (2013.01); *A61B 5/4088* (2013.01)

(58) Field of Classification Search
CPC ..... H04W 4/043; A61N 1/046; A61N 1/0484; G06F 19/34
See application file for complete search history.

(56) References Cited

U.S. PATENT DOCUMENTS

| | | | |
|---|---|---|---|
| 5,593,426 A | 1/1997 | Morgan et al. | |
| 5,752,976 A | 5/1998 | Duffin et al. | |
| 5,959,529 A | 9/1999 | Kail, IV | |
| 6,148,233 A | 11/2000 | Owen et al. | |
| 6,225,901 B1 | 5/2001 | Kail, IV | |
| 6,289,280 B1 | 9/2001 | Fernandez-Corbaton et al. | |
| 6,292,698 B1 | 9/2001 | Duffin et al. | |
| 6,402,691 B1 | 6/2002 | Peddicord et al. | |
| 6,405,083 B1 | 6/2002 | Rockwell et al. | |
| 6,602,191 B2 | 8/2003 | Quy | |
| 6,656,125 B2 | 12/2003 | Misczynski et al. | |
| 6,681,003 B2 | 1/2004 | Linder et al. | |
| 6,747,556 B2 | 6/2004 | Medema et al. | |
| 6,748,324 B2 | 6/2004 | Patwari et al. | |
| 6,790,178 B1 | 9/2004 | Mault et al. | |
| 6,937,150 B2 | 8/2005 | Medema et al. | |
| 6,957,102 B2 | 10/2005 | Silver et al. | |
| 6,980,112 B2 | 12/2005 | Nee | |
| 7,120,488 B2 | 10/2006 | Nova et al. | |
| 7,129,836 B2 | 10/2006 | Lawson et al. | |
| 7,231,258 B2 | 6/2007 | Moore et al. | |
| 7,289,029 B2 | 10/2007 | Medema et al. | |
| 7,289,844 B2 | 10/2007 | Misczynski et al. | |
| 7,396,330 B2 | 7/2008 | Banet et al. | |
| 7,769,465 B2 | 8/2010 | Matos | |
| 7,962,152 B2 | 6/2011 | Buerger et al. | |
| 7,986,998 B2 | 7/2011 | Hatlestad | |
| 8,086,320 B2 | 12/2011 | Saketkhou | |
| 8,180,457 B2 | 5/2012 | Matos | |
| 8,277,377 B2 | 10/2012 | Quy | |
| 8,334,768 B2 | 12/2012 | Eaton et al. | |
| 8,391,956 B2 | 3/2013 | Zellers et al. | |
| 8,419,644 B2 | 4/2013 | Eerden | |
| 8,447,626 B2 | 5/2013 | Sun et al. | |
| 8,473,065 B2 | 6/2013 | Matos | |
| 8,838,217 B2 | 9/2014 | Myr | |
| 8,868,330 B2 | 10/2014 | Park et al. | |
| 8,904,214 B2 | 12/2014 | Volpe et al. | |
| 9,013,350 B2 | 4/2015 | Alizadeh-Shabdiz | |
| 9,383,451 B2 | 7/2016 | Johnson | |
| 9,897,459 B2* | 2/2018 | Johnson | G16H 40/63 |
| 2002/0032470 A1 | 3/2002 | Linberg | |
| 2003/0025602 A1 | 2/2003 | Medema et al. | |
| 2003/0130793 A1 | 7/2003 | Patwari et al. | |
| 2003/0233129 A1 | 12/2003 | Matos | |
| 2005/0065445 A1 | 3/2005 | Arzbaecher et al. | |
| 2005/0186967 A1 | 8/2005 | Ozluturk | |
| 2006/0009238 A1 | 1/2006 | Stanco et al. | |
| 2006/0149322 A1 | 7/2006 | Merry et al. | |
| 2006/0284732 A1 | 12/2006 | Brock-Fisher | |
| 2007/0129769 A1 | 6/2007 | Bourget et al. | |
| 2008/0293431 A1 | 11/2008 | Buerger et al. | |
| 2009/0076343 A1 | 3/2009 | James et al. | |
| 2009/0164253 A1 | 6/2009 | Lyshkow | |
| 2009/0264948 A1 | 10/2009 | Tamura et al. | |
| 2009/0322513 A1 | 12/2009 | Hwang et al. | |
| 2009/0326595 A1 | 12/2009 | Brockway et al. | |
| 2011/0009813 A1 | 1/2011 | Rankers | |
| 2011/0051658 A1 | 3/2011 | Jin et al. | |
| 2011/0294515 A1 | 12/2011 | Chen et al. | |
| 2012/0089330 A1 | 4/2012 | Hesch et al. | |
| 2012/0112903 A1 | 5/2012 | Kaib et al. | |
| 2012/0157795 A1 | 6/2012 | Chiu et al. | |
| 2012/0252485 A1 | 10/2012 | Wolverton et al. | |
| 2013/0009783 A1 | 1/2013 | Tran | |
| 2013/0045759 A1 | 2/2013 | Smith | |
| 2013/0143595 A1 | 6/2013 | Moshfeghi | |
| 2013/0218053 A1 | 8/2013 | Kaiser et al. | |
| 2013/0304147 A1 | 11/2013 | Aoyama et al. | |
| 2013/0324868 A1 | 12/2013 | Kaib et al. | |
| 2013/0337827 A1 | 12/2013 | Grobman | |
| 2014/0100622 A1 | 4/2014 | Sullivan et al. | |
| 2014/0163334 A1 | 6/2014 | Volpe et al. | |
| 2014/0207371 A1 | 7/2014 | Johnson | |
| 2014/0274115 A1* | 9/2014 | Michalson | H04W 4/028 455/456.1 |
| 2014/0292534 A1 | 10/2014 | Stever et al. | |
| 2014/0379255 A1 | 12/2014 | Johnson | |
| 2015/0081216 A1* | 3/2015 | Bartels | G01C 21/26 701/532 |
| 2015/0265845 A1* | 9/2015 | Sullivan | A61N 1/3993 607/8 |

OTHER PUBLICATIONS

Sayed et al., "Network-Based Wireless Location," IEEE Signal Processing Magazine, XP011135184, IEEE Service Center, Piscataway, NJ, US, vol. 22, No. 4, pp. 24-40, Jul. 1, 2005.

International Search Report and Written Opinion from corresponding PCT Application Serial No. PCT/US2016/023718 dated Sep. 19, 2016.

\* cited by examiner

SYSTEMS AND METHODS OF DETERMINING LOCATION USING A MEDICAL DEVICE

RELATED APPLICATIONS

This application claims priority under 35 U.S.C. § 119(e) to U.S. Provisional Application Ser. No. 62/137,470, titled "SYSTEMS AND METHODS OF DETERMINING LOCATION USING A MEDICAL DEVICE," filed Mar. 24, 2015, which is hereby incorporated herein by reference in its entirety.

BACKGROUND

Technical Field

Aspects of the present disclosure relate to medical devices, and more particularly to apparatus and processes of determining location for medical devices.

Discussion

Medical devices monitor patients and/or administer therapy to patients. Some medical devices have a small physical footprint, are lightweight, and are therefore portable by patients, rescuers, or other medical personnel. Portable medical devices include, for example, defibrillators (such as ZOLL® X-Series® or E-Series® devices), automatic external defibrillators (AEDs) (such as ZOLL® AED Pro® devices), wearable defibrillators (such as ZOLL® LifeVest® devices), combinations thereof, and the like. Some of the portable medical devices may be assigned to patients while other portable medical devices may be unassigned. The patient assigned portable medical devices may be prescribed in in-patient and/or out-patient settings. Thus, portable medical devices may be used in a wide variety of indoor and outdoor environments.

SUMMARY

Aspects of the present disclosure provide for processes and apparatus for determining the location of one or more medical devices. For instance, in accordance with one example, a medical device is configured to accurately determine its location. In making this determination, the medical device executes a robust process that consistently and accurately determines the location of the medical device regardless of whether the device is located indoors, where global positioning system (GPS) signals are weak, or outdoors. For example, in some examples, the medical device is configured to employ one or more indoor positioning system (IPS) location determination processes to accurately determine the location of the patient. The medical device may be further configured to employ other location determination processes (e.g., location determination by GPS) and/or switch between the location determination processes based on environmental characteristics to increase the reliability of the location determination process within the current environment. Also, in some examples, the medical device is configured to transmit the location of the medical device to a remote system. For example, the medical device may transmit its location to a medical dispatcher or other medical personnel to assist the medical personnel in locating and providing medical care to the patient.

According to at least one aspect, a wearable medical device is provided. The wearable medical device includes a sensing electrode to sense an electrocardiogram signal of a patient, a therapy electrode to provide treatment to the patient, a garment to be worn about a torso of the patient and receive the sensing electrode and the therapy electrode, a motion detector to detect a movement of the medical device, and a controller coupled to the sensing electrode, the therapy electrode, and the motion detector, the controller being configured to track a location of the wearable medical device based on the detected movement of the medical device.

In one example, the controller is configured to track the location of the wearable medical device by dead reckoning. In one example, the motion detector includes a gyroscope, an accelerometer, or a magnetometer. In one example, the wearable medical device includes an antenna coupled to the controller and the controller is configured to transmit, via the antenna, the location of the wearable medical device to an external system.

In one example, the controller is configured to track the location of the wearable medical device at least in part by identifying a starting location of the wearable medical device, determining an estimated movement of the wearable medical device based on the detected movement of the medical device, and determining the location of the wearable medical device based on the starting location and the estimated movement.

In one example, the controller is configured to administer a physical activity test to the patient and measure a distance traveled by the patient during the physical activity test (e.g., a six minute walk test). In this example, the controller may be configured to monitor a gait of the patient during the physical activity test and determine a likelihood of the patient developing a form of dementia based on the gait of the patient. It is appreciated that the wearable medical device may include an antenna coupled to the controller and the controller may be configured to generate a patient report based on the administered physical activity test and transmit, via the antenna, the patient report to an external system.

In one example, the wearable medical device includes a memory coupled to the controller to store building map information and the controller is configured to track the location of the wearable medical device within a building based on the detected movement of the medical device and the building map information.

In one example, the wearable medical device includes an antenna coupled to the controller to receive location information. In this example, the controller may be configured to determine whether the location information is available from the antenna, determine the location of the wearable medical device based on the location information responsive to the location information being available, and determine the location of the wearable medical device based on the detected movement of the medical device responsive to the location information being unavailable. It is appreciated that the wearable medical device may include a switch to control a capability of the medical device to receive the location information from the antenna and the controller may be configured to determine, based on a state of the switch, the location of the wearable medical device from one of: the detected movement of the medical device and the location information. In addition, in some examples, the controller may be configured to attempt to determine the location of the wearable medical device based on the location information within a predetermined period of time and determine the location of the wearable medical device based on the detected movement of the device responsive to failing to determine the location of the wearable medical device based on the location information within the predetermined period of time. The location information may include, for example, a signal from a global positioning system, a BLUETOOTH beacon, a WLAN access point, or a radio frequency identification tag.

According to at least one aspect, a wearable medical device is provided. The wearable medical device includes a sensing electrode to sense an electrocardiogram signal of a patient, a therapy electrode to provide treatment to the patient, a garment to be worn about a torso of the patient and receive the sensing electrode and the therapy electrode, and a controller operatively coupled to the sensing electrode and the therapy electrode, the controller being configured to determine a current location of the wearable medical device based on a previous position of the medical device and at least a speed and a direction of movement of the wearable medical device.

In one example, the controller is configured to identify an elapsed time since the medical device was at the previous position. In this example, the controller may be configured to identify a distance traveled by the medical device based on the elapsed time and the previous speed of the medical device. It is appreciated that the controller may also be configured to identify the current location based on the distance traveled by the medical device and the previous location.

In one example, the controller is configured to identify the current location of the wearable medical device by dead reckoning. In one example, the wearable medical device includes a motion detector coupled to the controller and the controller is configured to identify the previous speed of the medical device based on detected motion of the medical device.

According to at least one aspect, an ambulatory medical device is provided. The ambulatory medical device includes a sensing electrode to sense an electrocardiogram signal of a patient, a memory to store building map information including a layout of a building, and a controller coupled to the sensing electrode and the memory. The controller may be configured to monitor cardiac events of the patient, track a location of the ambulatory medical device within the building, and generate a building map with a location history of the ambulatory medical device based on the building map information and the tracked location of the ambulatory medical device.

In one example, the controller is configured to track the location of the ambulatory medical device by dead reckoning. In one example, the ambulatory medical device includes a display coupled to the controller and the controller is configured to display, via the display, the building map with the location history of the ambulatory medical device. In one example, the ambulatory medical device includes an antenna coupled to the controller and the controller is configured to transmit, via the antenna, the building map with the location history of the ambulatory medical device to an external system. In one example, the ambulatory medical device is one of: a wearable defibrillator, an in-hospital defibrillator, and a mobile cardiac telemetry monitor.

In one example, the controller is configured to administer a physical activity test to the patient and track the location of the ambulatory medical device during the physical activity test (e.g., a six minute walk test). In this example, the controller may be configured to generate a patient report based on the administered physical activity test including a building map with a location history of the ambulatory medical device during the physical activity test. It is appreciated that the ambulatory medical device may include an antenna coupled to the controller and the controller may be configured to transmit, via the antenna, the patient report to an external system.

According to at least one aspect, an external ambulatory monitoring device is provided. The external ambulatory monitoring device includes at least one the sensing electrode configured to be disposed on a patient, at least one motion detector for detecting a movement of the device, and a location manager component. The location manager component may comprise at least one processor to track a location of the patient based on the detected movement of the device.

In one example, the at least one motion detector includes at least one of a gyroscope, an accelerometer, and a magnetometer. In one example, the location manager component transmits the location of the patient to an external system. In one example, the location manager component tracks the location of the patient at least in part by identifying a starting location of the patient, determining an estimated movement of the patient based on the detected movement of the device, and determining the location of the patient based on the starting location and the estimated movement.

In one example, the external ambulatory monitoring device includes a health manager component to administer a physical activity test to a patient and measure the distance traveled by the patient during the physical activity test. In addition, the health manager component may monitor a gait of the patient during the physical activity test based on the detected movement of the device and determine a likelihood of the patient getting at least one form of dementia based on the gait of the patient. In one example, the physical activity test includes a six minute walk test. In one example, the health manager component generates a patient report based on the administered physical activity test.

In one example, the external ambulatory monitoring device includes a memory storing building map information and wherein the location manager component tracks the location of the patient within a building based on the detected movement of the device and the building map information. In one example, the external ambulatory monitoring device includes at least one antenna for receiving location information.

In one example, the location manager component determines whether the location information is available from the at least one antenna, determines the location of the patient based on the location information responsive to the location information being available, and determines the location of the patient based on the detected movement of the device responsive to the location information being unavailable. In one example, the external ambulatory monitoring device includes a switch to control a capability of the medical device to receive the location information from the at least one antenna and wherein the location manager component determines, based on the state of the switch, the location of the patient from one of: the detected movement of the device and the location information. In one example, the location manager component attempts to determine the location of the patient based on the location information within a predetermined period of time and determines the location of the patient based on the detected movement of the device responsive to failing to determine the location of the patient based on the location information within the predetermined period of time. In one example, the location information includes a signal from at least one of a Global Positioning System, a Bluetooth® beacon, a WLAN access point, a light beacon, and a Radio Frequency Identification tag. In one example, the location manager component determines the location of the medical device based on the location information by at least one of Assisted GPS, Differential GPS, Wide Area Augmentation System GPS, and Defense Advanced GPS. In one example, the external ambulatory monitoring device comprises a wearable defibrillator.

According to at least one aspect, a method of determining a location of a patient using an external ambulatory monitoring device is provided. The method includes detecting a movement of the device by at least one motion detector and tracking, by the location manager component comprising at least one processor, a location of the patient based on the detected movement of the device.

In one example, the act of tracking the location of the patient includes identifying a starting location of the patient, determining an estimated movement of the patient based on the detected movement of the device, and determining the location of the patient based on the starting location and the estimated movement. In one example, the method includes administering a physical activity test to a patient and measuring the distance traveled by the patient during the physical activity test.

According to at least one aspect, a non-transitory computer readable medium storing executable instructions for determining a location of an external ambulatory monitoring device is provided. The executable instructions may include instructions that cause at least one processor to detect a movement of the device by at least one motion detector and track a location of the patient based on the detected movement of the device.

Still other aspects, examples, and advantages of these exemplary aspects are discussed in detail below. Moreover, it is to be understood that both the foregoing information and the following detailed description are merely illustrative examples of various aspects, and are intended to provide an overview or framework for understanding the nature and character of the claimed subject matter. Any example disclosed herein may be combined with any other example. References to "an example," "some examples," "an alternate example," "various examples," "one example," "at least one example," "this and other examples" or the like are not necessarily mutually exclusive and are intended to indicate that a particular feature, structure, or characteristic described in connection with the example may be included in at least one example. The appearances of such terms herein are not necessarily all referring to the same example.

Furthermore, in the event of inconsistent usages of terms between this document and documents incorporated herein by reference, the term usage in the incorporated references is supplementary to that of this document; for irreconcilable inconsistencies, the term usage in this document controls. In addition, the accompanying drawings are included to provide illustration and a further understanding of the various aspects and examples, and are incorporated in and constitute a part of this specification. The drawings, together with the remainder of the specification, serve to explain principles and operations of the described and claimed aspects and examples.

BRIEF DESCRIPTION OF DRAWINGS

The accompanying drawings are not intended to be drawn to scale. In the drawings, components that are identical or nearly identical may be represented by a like numeral. For purposes of clarity, not every component is labeled in every drawing. In the drawings.

DETAILED DESCRIPTION

Some examples disclosed herein generally relate to determining an indoor or outdoor location of a medical device. Location determination indoors is a challenging problem because of building infrastructure. Reinforced concrete, for example, highly attenuates and reflects electromagnetic waves, such as GPS or Global Navigation Satellite Systems (GNSS) signals emitted by satellites. Accordingly, in some examples, the medical device is capable of determining its location by various IPS techniques (e.g., processes that do not require GPS signals from satellites). In some examples, the medical device may use IPS processes (such as dead reckoning) in combination with GPS and/or GNSS location determination processes to accurately determine the location of the medical device irrespective of the environment. In addition, the location of the medical device may be transmitted to an external system. For example, the medical device may transmit the building address and floor where it and a patient are located to a medical dispatcher.

The examples of the methods and apparatuses discussed herein are not limited in application to the details of construction and the arrangement of components set forth in the following description or illustrated in the accompanying drawings. The methods and apparatuses are capable of implementation in other examples and of being practiced or of being carried out in various ways. Examples of specific implementations are provided herein for illustrative purposes only and are not intended to be limiting. In particular, acts, elements and features discussed in connection with any one or more examples are not intended to be excluded from a similar role in any other examples.

Also, the phraseology and terminology used herein is for the purpose of description and should not be regarded as limiting. Any references to examples or elements or acts of the systems and methods herein referred to in the singular may also embrace examples including a plurality of these elements, and any references in plural to any example or element or act herein may also embrace examples including only a single element. References in the singular or plural form are not intended to limit the presently disclosed systems or methods, their components, acts, or elements. The use herein of "including," "comprising," "having," "containing," "involving," and variations thereof is meant to encompass the items listed thereafter and equivalents thereof as well as additional items. References to "or" may be construed as inclusive so that any terms described using "or" may indicate any of a single, more than one, and all of the described terms.

Example Wearable Medical Device

Figure 1:
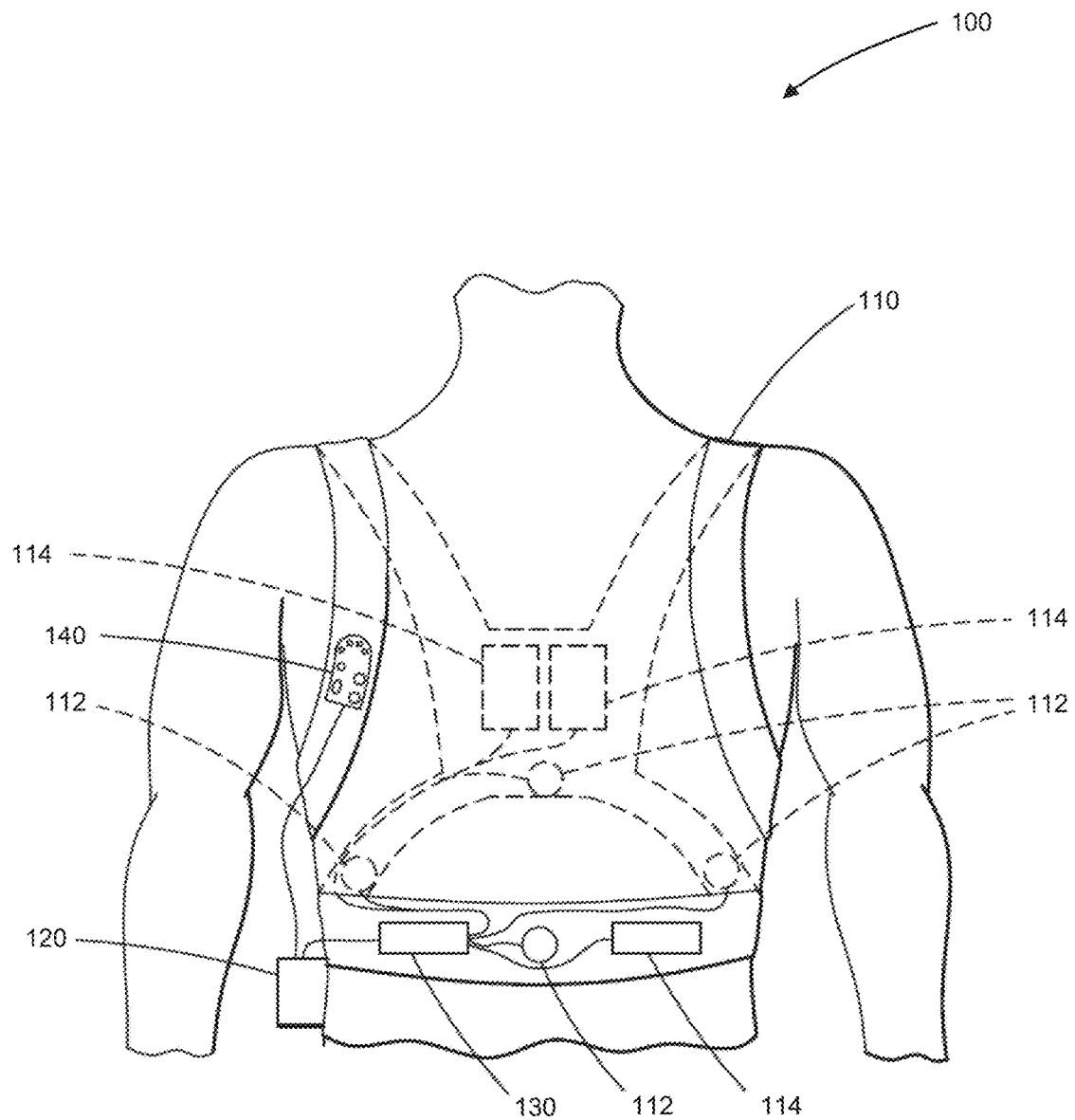
FIG. 1 is an illustration of one example of an ambulatory medical device.

In one example, the medical device is a wearable medical device that includes a garment (e.g., a vest or belt) that is worn by the patient. The wearable medical device monitors the patient's ECG with sensing electrodes, detects life-threatening arrhythmias, and delivers a cardioverting or defibrillating shock through therapy pads if treatment is necessary. FIG. 1 illustrates an example wearable medical device, such as a LifeVest® wearable cardioverter defibrillator available from ZOLL Medical Corporation of Chelmsford, Mass. As shown, the wearable medical device 100 includes a harness 110 having a pair of shoulder straps and a belt that is worn about the torso of a patient. The wearable medical device 100 includes a plurality of ECG sensing electrodes 112 that are attached to the harness 110 at various positions about the patient's body and electrically coupled to the sensor interface of the medical device controller 120 via a connection pod 130. The plurality of ECG sensing electrodes 112, which may be dry-sensing capacitance electrodes, are coupled to the medical device controller 120 to monitor the cardiac function of the patient and generally include a front/back pair of ECG sensing electrodes and a side/side pair of ECG sensing electrodes. Additional ECG sensing electrodes may be provided, and the plurality of ECG sensing electrodes 112 may be disposed at varying locations about the patient's body.

The wearable medical device 100 also includes a plurality of therapy electrodes 114 that are electrically coupled to the medical device controller 120 via the connection pod 130 and which are configured to deliver one or more therapeutic defibrillating shocks to the body of the patient, if it is determined that such treatment is warranted. The connection pod 130 electrically couples the plurality of ECG sensing electrodes 112 and the plurality of therapy electrodes 114 to the medical device controller 120, and may include electronic circuitry. The connection pod 130 may also include other electronic circuitry, such as a motion sensor or accelerometer through which patient activity may be monitored. It is appreciated that the wearable medical device 100 may be a monitoring only device and omit the therapy delivery capabilities and associated components including, for example, the therapy electrodes 114. In other embodiments, the wearable medical device 100 is a convertible wearable medical device that is capable of switching between a monitoring only wearable medical device and a wearable treatment device. In these embodiments, the various treatment components may be packaged into various modules that can be attached or removed from the wearable medical device as needed.

As shown in FIG. 1, the wearable medical device 100 also includes a user interface pod 140 that is electrically coupled to, or integrated in with, the user interface of the medical device controller 120. The user interface pod 140 can be attached to the patient's clothing or to the harness 110, for example, via a clip (not shown) that is attached to a portion of the interface pod 140. Alternatively, the user interface pod 140 may simply be held in a person's hand. For example, such a user interface pod 140 can be a smartwatch or a smartphone. In some examples, the user interface pod 140 may communicate wirelessly with the user interface of the medical device controller 120, for example, using a Bluetooth®, Wireless USB, ZigBee, Wireless Ethernet, GSM, or other type of communication interface.

The user interface pod 140 includes a number of buttons by which the patient, or a bystander can communicate with the medical device controller 120, and a speaker by which the medical device controller 120 may communicate with the patient or the bystander. For example, where the medical device controller 120 determines that the patient is experiencing cardiac arrhythmia, the medical device controller 120 may issue an audible alarm via a speaker on the medical device controller 120 or the user interface pod 140 alerting the patient and any bystanders to the patient's medical condition. The medical device controller 120 may also instruct the patient to press and hold one or more buttons on the user interface of the medical device controller 120 or on the user interface pod 140 to indicate that the patient is conscious, thereby instructing the medical device controller 120 to withhold the delivery of one or more therapeutic defibrillating shocks. If the patient does not respond, the device may determine that the patient is unconscious, and proceed with the treatment sequence, culminating in the delivery of one or more defibrillating shocks to the body of the patient.

Figure 2B:
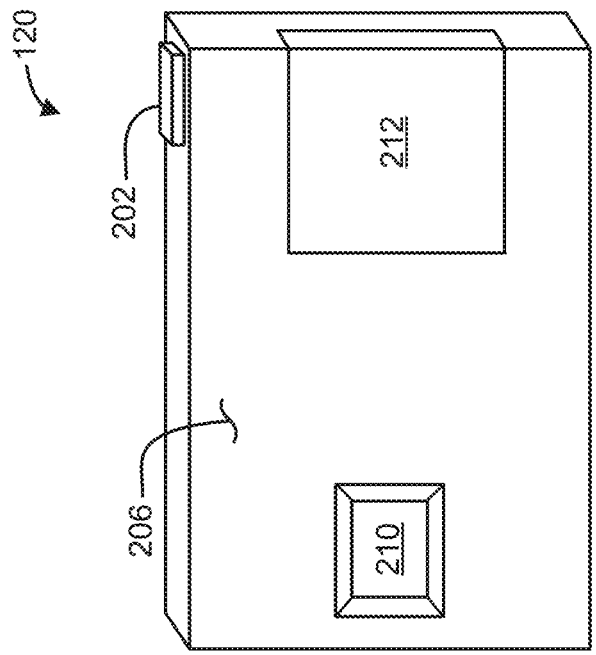
FIGS. 2A-2B are illustrations of one example of a medical device controller for an ambulatory medical device.
Figure 2A:
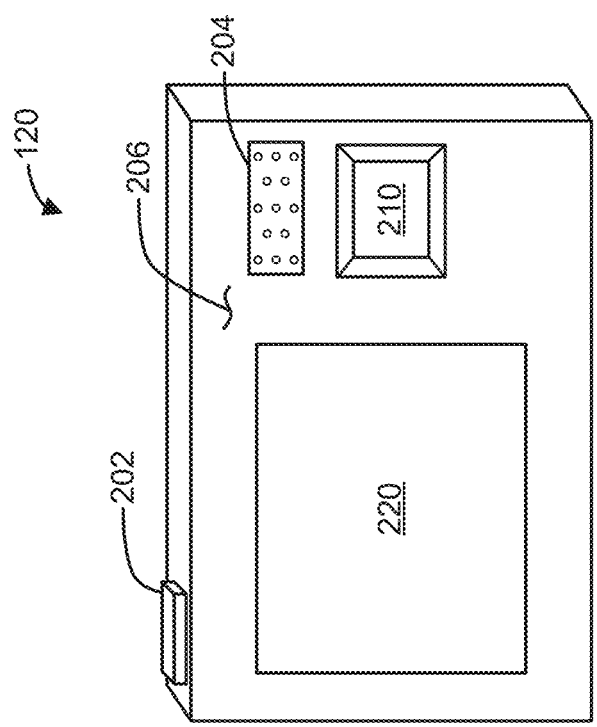

In another example, the functionality of the user interface pod 140 is integrated into the housing of the medical device controller 120. FIGS. 2A-2B illustrate such an example of the medical device controller 120. The controller 120 may be powered by a rechargeable battery 212. The rechargeable battery 212 may be removable from a housing 206 of the medical device controller 120 to enable a patient and/or caregiver to swap a depleted (or near depleted) battery 212 for a charged battery. The medical device controller 120 includes two response buttons 210 on opposing sides of the housing 206 of the medical device controller 120. As shown in FIGS. 2A-2B, the response buttons 210 are recessed to reduce the likelihood of accidental activation (e.g., a patient falling on the response button). The medical device controller 120 also includes, in this example, a display screen 220 and a speaker 204 to enable the communication of audible and visual stimuli to the patient. It is appreciated that the response buttons 210 do not have to be placed on opposing sides of the housing as illustrated in FIGS. 2A-2B. The response buttons 210, for example, may be located adjacent to each other in the housing the ambulatory medical device controller. The adjacent placement of the response buttons 210 may make it easier for individuals with smaller hands or less dexterity to engage the response buttons. The medical device controller 120 may further include a port 202 to removably connect sensing devices (e.g., ECG sensing electrodes 112) and/or therapeutic devices (e.g., therapy electrodes 114) to the medical device controller 120.

Another example wearable medical device is the ambulatory external defibrillator described in FIG. 1 of U.S. Pat. No. 8,904,214, titled "SYSTEM AND METHOD FOR CONSERVING POWER IN A MEDICAL DEVICE," filed Jul. 9, 2010 (hereinafter the "'096 application"), which is hereby incorporated herein by reference herein in its entirety. In at least one example, the ambulatory defibrillator 100 illustrated in FIG. 1 of the '096 application may employ the medical device controller 120, as disclosed in the present application, as a substitute for the portable treatment controller 200 described in the '096 application. In such an example, the ECG electrodes and therapy pads illustrated in FIG. 1 of the '096 application may be logically and physically coupled to the medical device controller 120. While some of the examples disclosed herein are directed to wearable medical devices, the systems and methods disclosed herein may be readily applied to other medical devices as described in more detail below.

Example Medical Device for Use in a Health Care Facility Setting

Figure 3A:
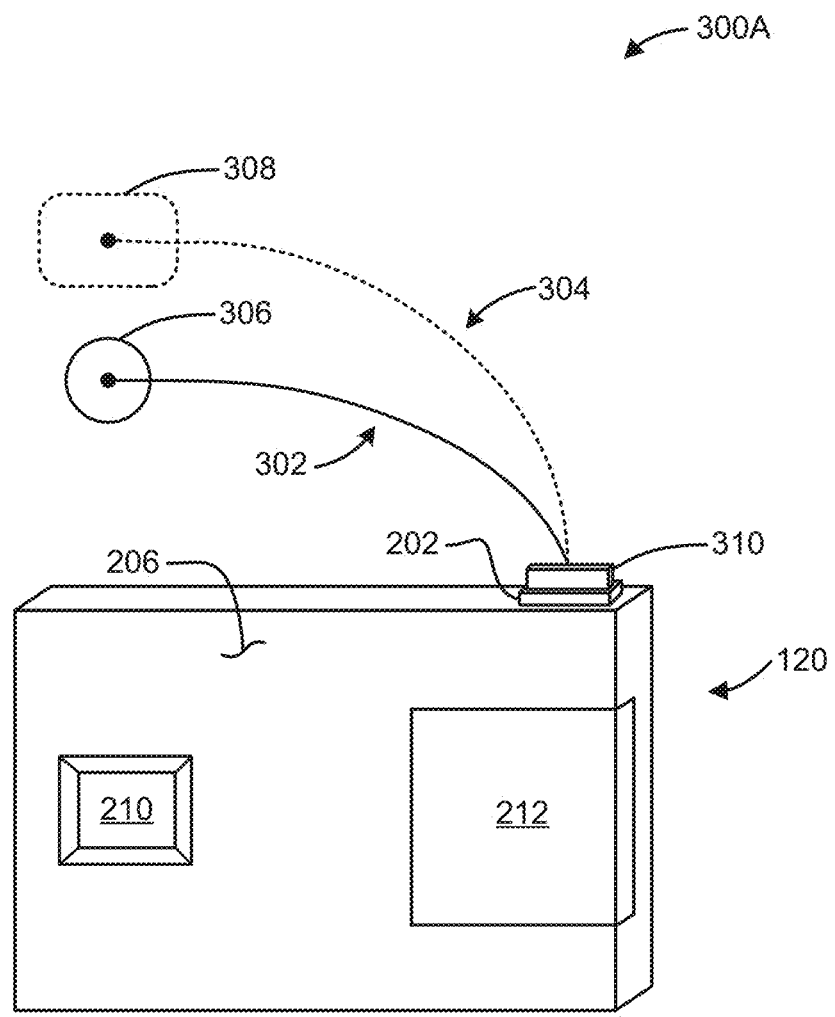
FIGS. 3A-3B are illustrations of example external medical devices.

In some examples, the medical device is constructed for use in an inpatient context, e.g., for use with patients admitted to a health care facility, such as, a hospital. FIG. 3A illustrates an example hospital based medical device 300A employing the medical device controller 120. The hospital based medical device 300A may be constructed to provide cardiac monitoring and/or treatment for patients in a hospital setting who may be, for example, bedridden and/or limited-mobility patients. As illustrated in FIG. 3A, the hospital based medical device 300A includes the medical device controller 120 and a sensing component 302. The sensing component 302 includes a connector 310 constructed to removably couple to the port 202 of the medical device controller 120. The sensing component 302 may detect information indicative of cardiac activity of the patient including, for example, ECG activity, tissue fluid, lung fluid, lung sounds, heart sounds, and/or patient activity. In some examples, the sensing component 302 includes one or more electrodes 306. The electrodes 306 may be stick-on adhesive electrodes constructed to attach to the patient. In some examples, the electrodes 306 may be detachable from a wire lead coupling the electrode 306 to the connector 310. Constructing the sensing component 302 to make the electrodes 306 detachable may enable the patient and/or caregiver to periodically (e.g., every 24-48 hours or more, as prescribed) replace the electrodes 306 without replacing the entire sensing component 302. For example, the electrodes 306 may be long term wear electrodes that are configured to be continuously worn by a patient for extended periods (e.g., 3 or more days).

In some examples, the hospital based medical device 300A may also include a treatment component 304 to provide treatment to the patient. The treatment component 304 may include, for example, a therapy pad 308 configured to attach to the patient. The treatment component 304 may be connected to the same connector 310 as the sensing component 302 and/or employ a separate connector that is capable of coupling to the connector 310. It is appreciated that the treatment component 304 may be integrated into the sensing component 302 in a combined sensing-treatment component. The combined sensing-treatment component may include an electrode with integrated sensing and treatment delivery capabilities as described in the '096 publication.

Example Monitoring Medical Device

In some examples, the medical device may be a patient monitoring device such as a mobile cardiac telemetry (MCT) monitor. For example, such a patient monitoring device may be configured to monitor one or more physiological parameters of a patient. For example, a patient monitor may include a cardiac monitor for monitoring a patient's cardiac information. Such cardiac information can include, without limitation, heart rate, ECG data, heart sounds data from an acoustic sensor, and other cardiac data. In addition to cardiac monitoring, the patient monitor may perform monitoring of other relevant patient parameters, including glucose levels, blood oxygen levels, lung fluids, lung sounds, and blood pressure.

An example cardiac monitoring medical device (e.g., a cardiac monitor) may be similar to the wearable medical device 100 and/or the hospital based medical device 300A described above with reference to FIGS. 1, 2A, 2B, and 3A and omit, for example, the therapy electrodes 114 and/or the therapy pad 308. In some implementations, the cardiac monitor is capable of and designed for being worn by a patient who is at risk of developing cardiac problems, but who does not yet meet criteria to be outfitted with a medical device that includes a treatment component (e.g., a defibrillator).

In some implementations, the patient can interact with a user interface of the cardiac monitor to identify one or more patient symptoms. The user interface may include a touch-screen that provides a drop down menu or check list which, in turn, allows the patient to select a particular symptom from a list of alternatives. Options for patient systems can include one or more of: feeling a skipped beat, shortness of breath, light headedness, racing heart rate, fatigue, fainting, chest discomfort, weakness, dizziness, and/or giddiness. In addition, the patient can select a level of activity (e.g., light activity, moderate activity, rigorous activity, etc.) that he or she was performing when the symptom occurred. In some implementations, in response to the selection by the patient, the cardiac monitor can cause a portion of patient physiological information (e.g., in the form of a cardiac signal) to be captured for a length of time that is based on when the symptom was experienced. For example, the cardiac monitor can cause a portion of an ECG signal of the patient to be captured. The portion of the ECG signal that is captured can be associated with the reported symptom and patient information. It is appreciated that the captured portion of the ECG signal and/or the associated symptoms may be stored locally for later review and/or wireless transmitted to another device for review by medical personnel (e.g., a physician).

Thus, the cardiac monitor may be prescribed so that continuous and/or event-based data can be sent from the cardiac monitor to a remote server. A caregiver can access the data from the remote server and determine whether the patient is experiencing or has experienced a cardiac problem. In some implementations, after determining that the patient is experiencing a cardiac problem, the caregiver may instruct the patient to begin wearing a medical device with treatment capabilities.

Example Automated Medical Device

Figure 3B:
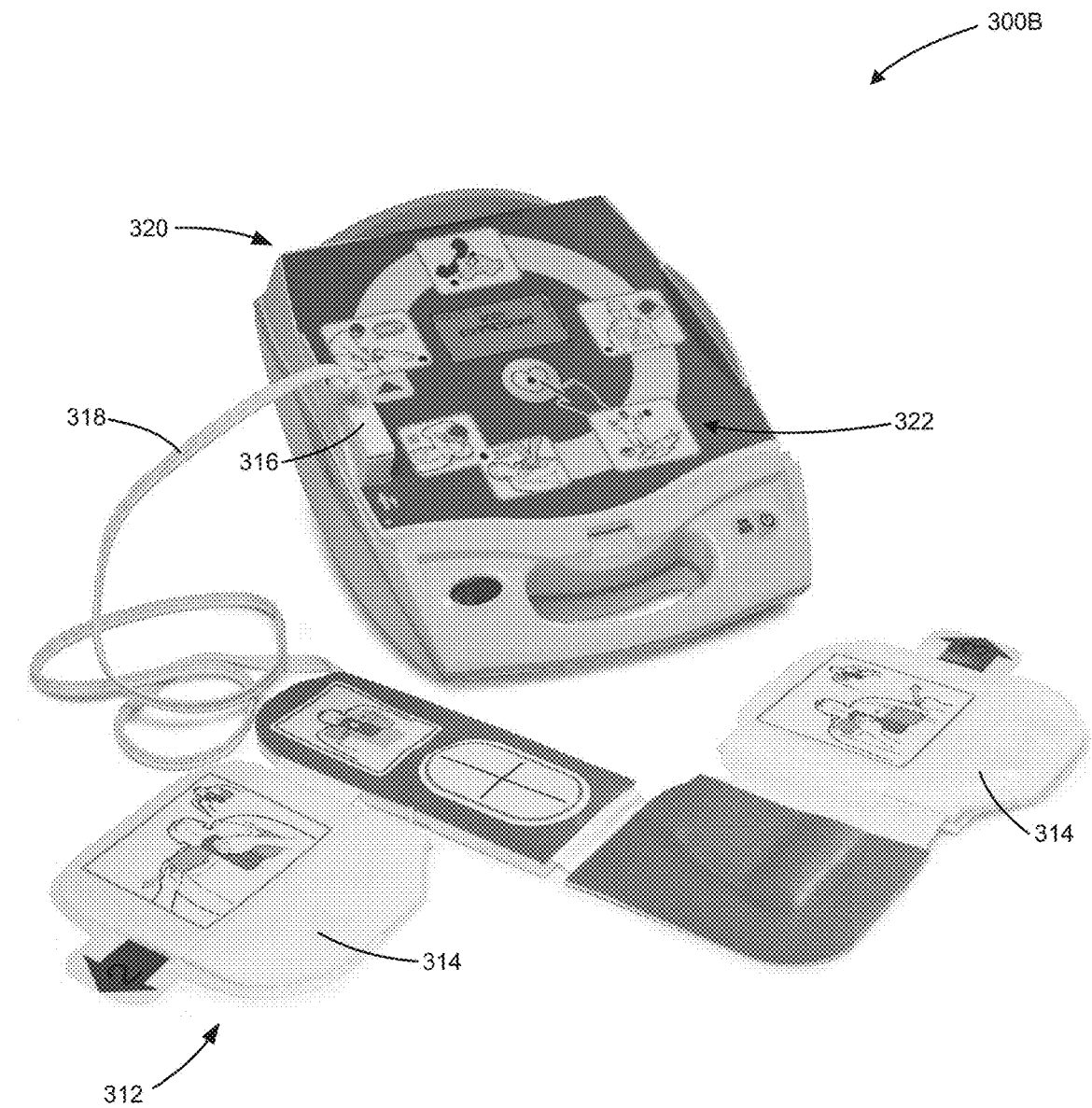

In one example, the medical device is an AED. AEDs are small portable defibrillators that are capable of monitoring cardiac rhythms, determining when a defibrillating shock is necessary, and administering the defibrillating shock either automatically, or under the control of a trained rescuer (e.g., an EMT or other medically training personnel). The AED, in addition, may be configured to provide counseling to an operator as to how to perform cardiopulmonary resuscitation (CPR). FIG. 3B illustrates an AED, such as an AED available from ZOLL Medical Corporation of Chelmsford, Mass. As shown, the AED 300B includes a medical device controller 320 and an electrode assembly 312.

The electrode assembly 312 includes one or more electrodes 314 (e.g., ECG sensing electrode, therapy electrodes, and/or combined ECG sensing and therapy electrodes), a connector 316, wiring 318 electrically coupling the connector 316 to the one or more electrodes 314. As shown in FIG. 3B, the connector 316 is configured to couple the electrode assembly 312 to the medical device controller 320.

The medical device controller 320 of the AED 300B is configured to detect the cardiac rhythm of the patient and provide defibrillating shocks to the patient as appropriate. This process may be similar to the process described with regard to medical device controller 120 of the ambulatory medical device 100. The user interface 322 of the AED 300B may include a variety of components configured to communicate with the operator including, but not limited to, a display screen, a speaker, and one or more buttons. In this example, the AED 300B includes a display screen to display notifications to an operator. The notifications may provide instructions to the operator regarding the proper administration of CPR to the patient. The notifications on the display may be accompanied by audible alerts from the speaker to further assist the operator in administering CPR to the patient.

According to various examples, the AED 300B and the wearable medical device 100 utilize a network interface of the medical device controllers 120 and 320, respectively, to determine location information and transmit the location information to the appropriate medical personnel via various devices including, for example, various wearable devices. While some of the examples disclosed herein are directed to medical devices for cardiac monitoring and treatment, other examples are directed to other types of medical devices that compute their location through a variety of processes executed by a medical device controller.

Example Medical Device Controller

Figure 4:
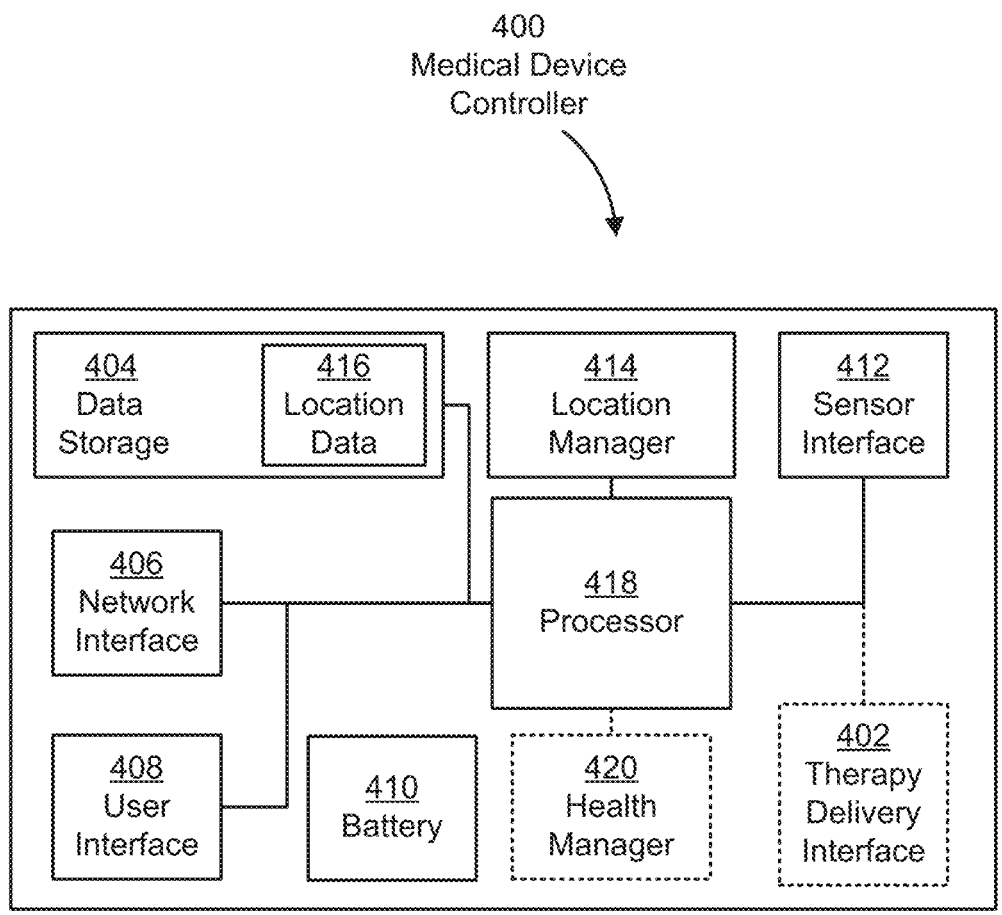
FIG. 4 is a functional schematic of one example of a medical device controller.

FIG. 4 illustrates a medical device controller 400 that is configured to monitor a patient and the patient's environment for events of interest and to determine the location of the medical device (or, for example, in the case of the wearable defibrillator, the location of the patient). The medical device controller 400 may, for example, be configured for use in a wearable medical device (e.g., medical device controller 120) or an AED (e.g., medical device controller 320). As shown in FIG. 4, the medical device controller 400 includes a processor 418, a sensor interface 412, a location manager 414, a health manager 420, a therapy delivery interface 402, data storage 404, a communication network interface 406, a user interface 408, and a battery 410. The data storage 404 includes location data 416. Further, in this illustrated example, the battery 410 is a rechargeable 3 cell 4200 mAh lithium ion battery pack that provides electrical power to the other device components with a minimum 44 hour runtime between charges. It is appreciated that the battery capacity, runtime, and type (e.g., lithium ion, nickel-cadmium, or nickel-metal hydride) may be changed to best fit the specific application of the medical device controller 400.

According to the example illustrated in FIG. 4, the processor 418 is coupled to the sensor interface 412, the therapy delivery interface 402, the data storage 404, the network interface 406, and the user interface 408. The processor 418 performs a series of instructions that result in manipulated data which are stored in and retrieved from the data storage 404. According to a variety of examples, the processor 418 is a commercially available processor such as a processor manufactured by Texas Instruments, Intel, AMD, Sun, IBM, Motorola, Freescale, and ARM Holdings. However, the processor 418 may be any type of processor, multiprocessor or controller, whether commercially available or specially manufactured. For instance, according to one example, the processor 418 may include a power conserving processor arrangement such as described in the '096 application. In another example, the processor 418 is an Intel® PXA270.

In addition, in some examples, the processor 418 may be configured to execute a conventional operating system. The operating system may provide platform services to application software, such as some examples of the location manager 414 which is discussed further below. These platform services may include inter-process and network communication, file system management and standard database manipulation. One or more of many operating systems may be used, and examples are not limited to any particular operating system or operating system characteristic. For instance, operating systems can include a Windows based operating system, OSX, or other operating systems. For instance, in some examples, the processor 418 may be configured to execute a real-time operating system (RTOS), such as RTLinux, or a non-real time operating system, such as BSD or GNU/Linux.

In some examples, the location manager 414 is configured to determine the location of the medical device or patient equipped with the medical device. Particular examples of the processes performed by the location manager 414 are discussed further below with reference to the Location Determination Processes section and FIGS. 5-8. For example, the location manager 414 may employ various antennas to receive GPS signals, other satellite navigation systems, and/or various motion detectors (e.g., accelerometers, magnetometers, and gyroscopes), including various IPS solutions as described below, to measure the movement of the patient and/or the medical device along with corresponding software. For example, the location manager may include an inertial measurement unit (IMU) that can measure and report a patient's movement, velocity, and orientation, using a combination of accelerometers, gyroscopes, and magnetometers. It is appreciated that the various location determination processes disclosed herein may be combined with other location determination processes to improve the accuracy of the determined location.

Figure 8:
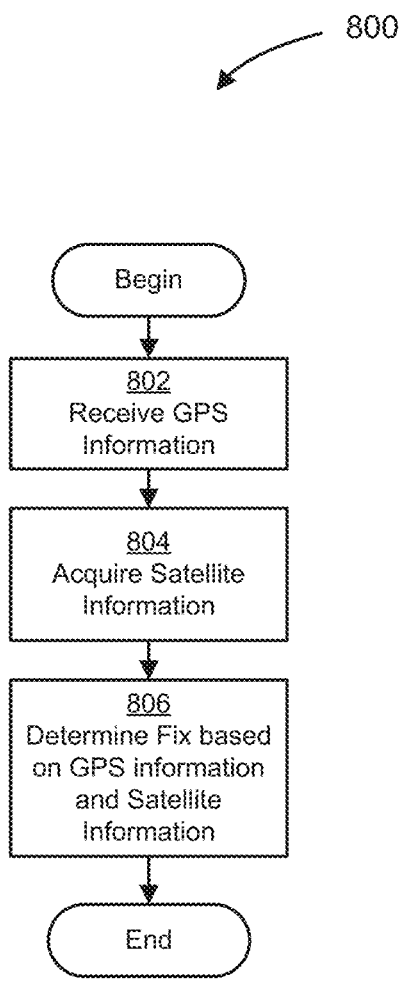
FIG. 8 is a flowchart of another example process for determining the location of a medical device.

In some examples, the dead reckoning and/or the assisted GPS (A-GPS) location determination processes described below with references to FIGS. 6 and 8, respectively, may be employed as part of a hierarchy of location information sources as described in U.S. patent application Ser. No. 14/308,368, titled "SYSTEMS AND METHODS OF DETERMINING LOCATION USING A MEDICAL DEVICE," filed Jun. 18, 2014 (hereinafter the "'368 application"), which is hereby incorporated herein by reference herein in its entirety. In these examples, the medical device may determine its location by a location determination process at the top of the hierarchy (e.g., a GPS location determination process) and proceed down the hierarchy employing other location determination processes to improve the accuracy of the determined location. The medical device may automatically adjust the determined location of the medical device as new sources of location information become available.

As illustrated in FIG. 4, in some examples, the health manager 420 can be configured to monitor various physiological parameters associated with the patient. The health manager 420 may also administer physical activity tests to the patient as is described further below with reference to FIG. 9. These physical activity tests may facilitate the medical device controller 400 to access the condition of the patient and/or provide treatment to the patient as appropriate.

The location manager 414 and/or the health manager 420 may be implemented using hardware or a combination of hardware and software. For instance, in one example, the location manager 414 and/or the health manager 420 is implemented as a software component that is stored within the data storage 412 and executed by the processor 418. In this example, the instructions included in the location manager 414 and/or the health manager 420 program the processor 418 to determine the location of the medical device. In other examples, the location manager 414 and/or the health manager 420 may be an application-specific integrated circuit (ASIC) that is coupled to the processor 418 and tailored to determine the location of the medical device.

Thus, examples of the location manager 414 and/or the health manager 420 are not limited to a particular hardware or software implementation.

In some examples, the components disclosed herein, such as the location manager 414, may read parameters that affect the functions performed by the components. These parameters may be physically stored in any form of suitable memory including volatile memory, such as RAM, or non-volatile memory, such as a flash memory or magnetic hard drive. In addition, the parameters may be logically stored in a propriety data structure, such as a database or file defined by a user mode application, or in a commonly shared data structure, such as an application registry that is defined by an operating system. In addition, some examples provide for both system and user interfaces, as may be implemented using the user interface 408, that allow external entities to modify the parameters and thereby configure the behavior of the components.

The data storage 404 includes a computer readable and writeable nonvolatile data storage medium configured to store non-transitory instructions and data. In addition, the data storage 404 includes processor memory that stores data during operation of the processor 418. In some examples, the processor memory includes a relatively high performance, volatile, random access memory such as dynamic random access memory (DRAM), static memory (SRAM) or synchronous DRAM. However, the processor memory may include any device for storing data, such as a non-volatile memory, with sufficient throughput and storage capacity to support the functions described herein. According to several examples, the processor 418 causes data to be read from the nonvolatile data storage medium into the processor memory prior to processing the data. In these examples, the processor 418 copies the data from the processor memory to the non-volatile storage medium after processing is complete. A variety of components may manage data movement between the non-volatile storage medium and the processor memory and examples are not limited to particular data management components. Further, examples are not limited to a particular memory, memory system or data storage system.

The instructions stored on the data storage 404 may include executable programs or other code that can be executed by the processor 418. The instructions may be persistently stored as encoded signals, and the instructions may cause the processor 418 to perform the functions described herein. The data storage 404 also may include information that is recorded, on or in, the medium, and this information may be processed by the processor 418 during execution of instructions. The medium may, for example, be optical disk, magnetic disk or flash memory, among others, and may be permanently affixed to, or removable from, the medical device controller 400.

In some examples, the location data 416 includes data used by the location manager 414 to determine the location of the medical device. For example, the location data 416 may include various maps (e.g., street maps and building maps). The various maps may be employed by the location manager 414 to determine, for example, a street address associated with the current location of the medical device. The various maps may also be employed by the location manager 414 to determine the current location of the medical device within a building (e.g. in the triage room in a hospital on the first floor). An example building map that may be stored in the location data 416 is illustrated below with reference to FIG. 10. As illustrated in FIG. 4, the location manager 414 and the location data 416 are separate components. However, in other examples, the location manager 414 and the location data 416 may be combined into a single component or re-organized so that a portion of the data included in the location manager 414, such as executable code that causes the processor 418 to determine the location of the medical device, resides in the location data 416, or vice versa. Such variations in these and the other components illustrated in FIG. 4 are intended to be within the scope of the examples disclosed herein.

The location data 416 may be stored in any logical construction capable of storing information on a computer readable medium including, among other structures, flat files, indexed files, hierarchical databases, relational databases, or object oriented databases. These data structures may be specifically configured to conserve storage space or increase data exchange performance. In addition, various examples organize the location data 416 into particularized and, in some cases, unique structures to perform the functions disclosed herein. In these examples, the data structures are sized and arranged to store values for particular types of data, such as integers, floating point numbers, character strings, arrays, linked lists, and the like.

In some examples, the location manager 414 and/or the associated location data 416 can be located in a device separate from the medical device controller 400. In these examples, such a location determination device may include location manager 414 and determine the location of the medical device. The resulting location determined by the location manager 414 may be provided to the medical device controller 400 by an interface (e.g., via a USB port of the medical device). The location determination device may include various hardware components to receive and process location information. For example, the location determination device may include various antennas to receive GPS signals, other satellite navigation systems, and/or various motion detectors (e.g., accelerometers, magnetometers, and gyroscopes) to measure the movement of the medical device in addition to a processor to execute instructions included within the location manager 414. Thus, the location manager 414 may be located outside the medical device controller 400.

As shown in FIG. 4, the medical device controller 400 includes several system interface components 402, 406, and 412. Each of these system interface components is configured to exchange, i.e. send or receive, data with one or more specialized devices that may be located within the housing of the medical device controller 400 or elsewhere. The components used by the interfaces 402, 406, and 412 may include hardware components, software components or a combination of both. Within each interface, these components physically and logically couple the medical device controller 400 to the specialized devices. This physical and logical coupling enables the medical device controller 400 to communicate with and, in some instances, power or control the operation of the specialized devices. These specialized devices may include physiological sensors, therapy delivery devices, and computer networking devices.

According to various examples, the hardware and software components of the interfaces 402, 406 and 412 implement a variety of coupling and communication techniques. In some examples, the interfaces 402, 406, and 412 use leads, cables or other wired connectors as conduits to exchange data between the medical device controller 400 and specialized devices. In other examples, the interfaces 402, 406, and 412 communicate with specialized devices using wireless technologies such as radio frequency or infrared technology. The software components included in the interfaces 402, 406, and 412 enable the processor 418 to communicate with specialized devices. These software components may include elements such as objects, executable code, and populated data structures. Together, these software components provide software interfaces through which the processor 418 can exchange information with specialized devices. Moreover, in at least some examples where one or more specialized devices communicate using analog signals, the interfaces 402, 406, and 412 further include components configured to convert analog information into digital information, and vice versa, to enable the processor 418 to communicate with specialized devices.

As discussed above, the system interface components 402, 406, and 412 shown in the example of FIG. 4 support different types of specialized devices. For instance, the components of the sensor interface 412 couple the processor 418 to one or more physiological sensors such as a body temperature sensors, respiration monitors, and electrocardiogram (ECG) sensing electrodes, one or more environmental sensors such as atmospheric thermometers, airflow sensors, video sensors, light sensors, audio sensors, GPS locators, and hygrometers, or one or more motion detection sensors such as altimeters, accelerometers, and gyroscopes. In these examples, the sensors may include sensors with varying sampling rates, including wireless sensors.

In some examples, the system interface components of the medical device controller 400 gather location information from various sources for the location manager 414. For example, the sensor interface 412 may employ various motion detection devices (e.g., pedometers, accelerometers, magnetometers, and/or gyroscopes) to determine the location of the medical device by, for example, one or more dead reckoning processes as described further below with reference to FIG. 6A. A suitable motion detector may include the iNEMO® M1 manufactured by STMicroelectronics. The iNEMO-M1 is a multi-axis inertial system including Microelectromechanical Systems (MEMS) sensors with an embedded microcontroller to receive and process information from the MEMS sensors (e.g., a 3-axis magnetometer, a 3-axis accelerometer, or a 3-axis gyroscope). The microcontroller employs information from the MEMS sensors to determine motion information including, for example, quaternions (e.g., a representation of orientation, direction, and rotation), heading, pitch, roll, yaw, linear acceleration, and/or gravity. It is appreciated that other motion detection devices may be employed to generate motion information. For example, motion detection devices may be employed with integrated GPS location capabilities. These devices may merge motion information with location information from one or more GPS receiving systems to determine location more accurately in urban environments. An example motion detection device with integrated GPS capabilities includes the BCM4752 manufactured by Broadcom® and the SiRFusion® manufactured by CSR®.

In some examples, the motion information generated by the motion detection devices may be processed by the medical device controller 400 to determine a medical condition of the patient. For example, the motion information may be acquired as part of a physical activity test (e.g., a six minute walk test) administered to the patient as described further below with reference to FIG. 9. The motion information may be processed to monitor the gait of the patient while the patient walks. The gait of a patient may be used, for example, as a potential indicator for Alzheimer's disease as described in Publication "Quantitative Gait Dysfunction and Risk of Cognitive Decline and Dementia" published by the Journal of Neurology, Neurosurgery, and Psychiatry in 2007, which is hereby incorporated herein by reference in its entirety. In particular, patients with a slower forward velocity and a slower cadence (e.g., steps per minute) are more likely to develop Alzheimer's disease. It is appreciated that the gait of a patient may be employed to diagnose other medical conditions including, for example, other forms of dementia.

Returning to FIG. 4, the components of the therapy delivery interface 402 couple one or more therapy delivery devices, such as capacitors, defibrillator electrodes, pacing electrodes or mechanical chest compression devices, to the processor 418. It is appreciated that the functionality of the therapy delivery interface 402 may be incorporated into the sensor interface 412 to form a single interface coupled to the processor 418. In addition, the components of the network interface 406 couple the processor 418 to a computer network via a networking device, such as a bridge, router or hub. According to a variety of examples, the network interface 406 supports a variety of standards and protocols, examples of which include USB (via, for example, a dongle to a computer), TCP/IP, Ethernet, Wireless Ethernet, Bluetooth, ZigBee, M-Bus, CAN-bus, IP, IPV6, UDP, DTN, HTTP, HTTPS, FTP, SNMP, CDMA, NMEA and GSM. It is appreciated that the network interface 406 of medical device controller 400 may enable communication between other medical device controllers within a certain range.

To ensure data transfer is secure, in some examples, the medical device controller 400 can transmit data via the network interface 406 using a variety of security measures including, for example, TLS, SSL or VPN. In other examples, the network interface 406 includes both a physical interface configured for wireless communication and a physical interface configured for wired communication. According to various examples, the network interface 406 enables communication between the medical device controller 400 and a variety of personal electronic devices including, for example, computer enabled glasses, wristwatches, and earpieces.

In one example, the network interface 406 is also capable of transmitting and/or receiving information to assist in medical device location determination. This may be accomplished through one or more antennas integrated with or coupled to the network interface 406, and consequently coupled to the processor 418. For example, the one or more antennas may receive GPS signals from external sources (e.g., satellites) to determine the location of the medical device with a given level of accuracy and/or used to determine the current time. The GPS signals received by the antennas may be analyzed by the processor 418 to determine the location of the medical device. In other examples, the medical device controller 400 may, via the network interface 406 and/or the sensor interface 412, be communicatively coupled to a GPS receiver module. The GPS receiver module may include the appropriate components to receive GPS signals, determine the location of the medical device based on the GPS signals, and provide the determined location to the medical device controller 400. It is appreciated that various GPS components (e.g., antennas) may be used in the medical device and/or the GPS receiver module based on the particular type, or combination of types, of GPS employed. Various GPS systems include, for example, high sensitivity GPS, Differential Global Positioning System (DGPS), Wide Area Augmentation System (WAAS), and Defense Advanced GPS. In addition, the GPS receive module may be capable of receiving and analyzing signals from local GPS like systems including, for example, the GPS like signals provided by a LocataLite® transceiver manufactured by Locata®.

It is appreciated that the systems described above with regard to connecting to various networks (e.g., wireless Ethernet or Bluetooth) may be used as probes to find known reference points within a given range. For example, the medical device controller 400 may detect a WLAN access point or a cellular network tower with known positions stored in a database accessible by the medical device controller 400. The medical device controller 400 may be able to determine its location at least in part by determining the distance between the medical device controller and the known location of the WLAN access point or cellular network tower. This may be accomplished at least in part by analyzing the signal strength of the WLAN access point or the cellular network tower.

It is appreciated that the medical device location computation may be performed in a collaborative fashion with the central server to minimize the computations performed by the medical device controller as described in U.S. patent application Ser. No. 14/158,027, titled "SYSTEMS AND METHOD FOR DETERMINING SPATIAL LOCATIONS OF PATIENT DATA GATHERING DEVICES," filed on Jan. 17, 2014, which is hereby incorporated herein by reference in its entirety. For example, the medical device may transmit the detected sources and their respective signal strengths. The central server may then compute the location of the medical device by analyzing the signal strengths and coordinates associated with the sources. The computed medical device location may then transmit to the medical device or a remote system (e.g., a remote system operated by medical personnel).

Thus, the various system interfaces incorporated in the medical device controller 400 allow the device to interoperate with a wide variety of devices in various contexts. For instance, some examples of the medical device controller 400 are configured to perform a process of sending critical events and data to a centralized server via the network interface 406. An illustration of a process in accord with these examples is disclosed in U.S. Pat. No. 6,681,003, titled "DATA COLLECTION AND SYSTEM MANAGEMENT FOR PATIENT-WORN MEDICAL DEVICES," and issued on Jan. 20, 2004, which is hereby incorporated herein by reference in its entirety.

As illustrated in FIG. 4, the therapy delivery interface 402 is optional and may not be included in every example. For instance, a heart rate monitor may employ the medical device controller 400 to issue alarms but may not include a therapy delivery interface 402 to treat cardiac abnormalities. Similarly, an ambulatory defibrillator may include the medical device controller 400 to provide alarm functionality but may not include a network interface 406 where, for example, the ambulatory defibrillator is designed to rely on the user interface 408 to announce alarms.

The user interface 408 shown in FIG. 4 includes a combination of hardware and software components that allow the medical device controller 400 to communicate with an external entity, such as a patient or other user. These components may be configured to receive information from actions such as physical movement, verbal intonation, or thought processes. In addition, the components of the user interface 408 can provide information to external entities. Examples of the components that may be employed within the user interface 408 include keyboards, mouse devices, trackballs, microphones, electrodes, touch screens, printing devices, display screens, and speakers. In some examples, the electrodes include an illuminating element, such as an LED. In other examples, the printing devices include printers capable of rendering visual or tactile (Braille) output.

The medical device controller 400 has a variety of potential applications and is well suited to devices that notify external entities of a variety of events, some of which may require a predetermined response from the external entity. Predetermined responses may include any response that is appropriate given the event being reported. Predetermined responses may include acknowledgment of the alarm, entry of information indicating that the alarm is being addressed and rectification of the event or condition that triggered the alarm. Examples of devices to which the medical device controller 400 is well suited include various cardiac monitoring devices and critical care medical devices, such as a wearable ambulatory external defibrillator, an AED, or a mechanical chest compression device, such as the Autopulse® system from ZOLL Medical Corporation of Chelmsford, Mass.

Example Medical Device Location Determination Processes

Figures 5A, 5B:
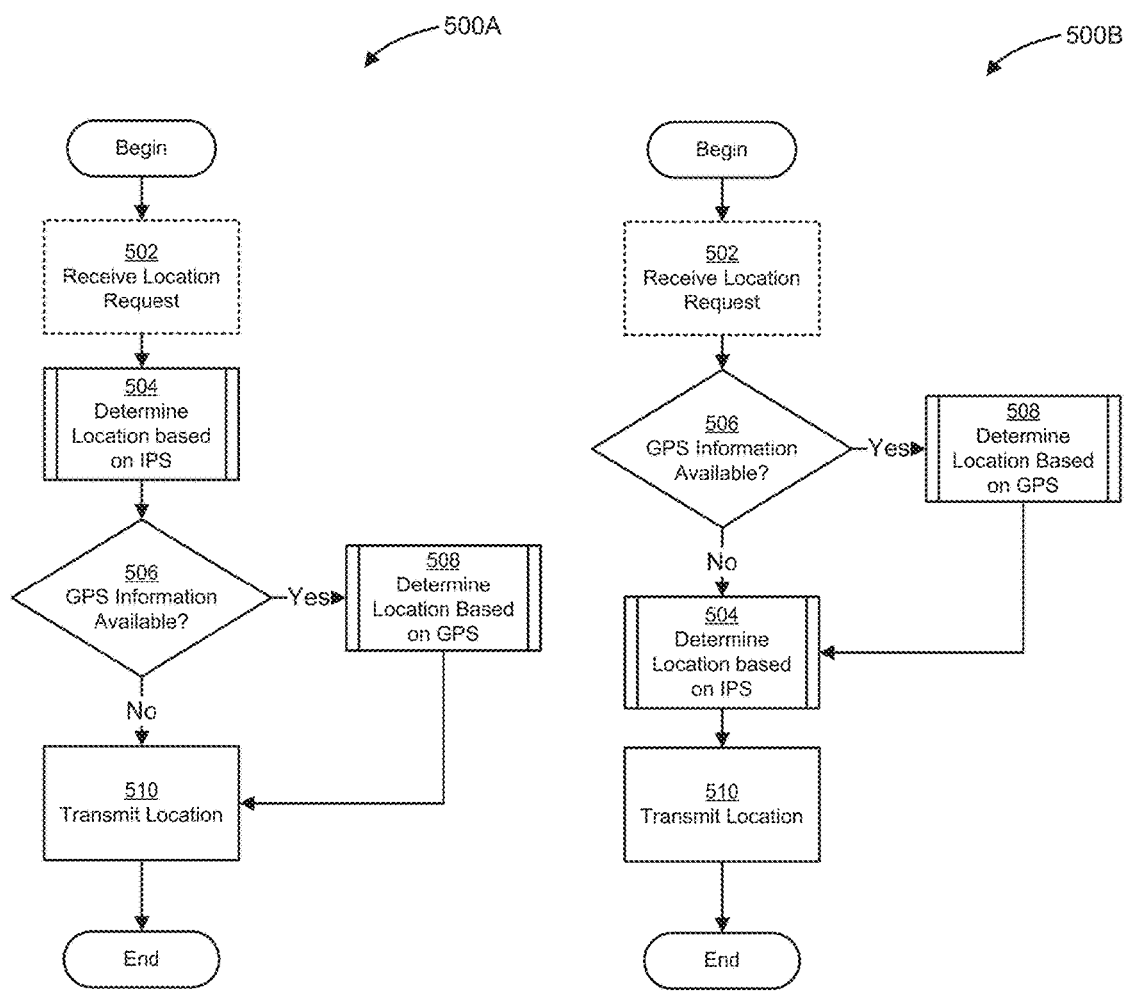
FIGS. 5A-5B are flowcharts of example processes for determining and transmitting the location of a medical device.

Various examples implement and enable processes through which a medical device determines and transmits its location. FIG. 5A illustrates one such process 500A that includes acts of determining the location based on IPS 504, determining whether GPS information is available 506, determining the location based on GPS 508, and transmitting the location 510. Process 500A may also include optional act 502 of receiving a location request. It is appreciated that the process 500A may be repeated as necessary to update the location of the medical device as the patient moves and/or new location information sources become available.

In optional act 502, the medical device receives a location request from another device. For example, the medical device may receive a location request from a cellular network via a network interface of the medical device. It is appreciated that other information may be employed to trigger the medical device to perform process 500. For example, the medical device may perform process 500 at predetermined intervals to periodically provide location updates to an external system. Another example event that may trigger process 500 includes the detection of a life threatening event. For example, the medical device may detect that the patient is experiencing an arrhythmia and/or has fallen due to a loss of consciousness.

In act 504, the medical device determines the location of the medical device by one or more IPS processes. In some examples, IPS processes include triangulating the location of the medical device based on signals emitted by one or more beacons with known locations. For example, the medical device may receive a signal from one or more Bluetooth® beacons with known locations, determine a distance between the device and the beacon based on the received signal strength, and determine the location of the medical device based on the known of the beacons and the known distance between the medical device and each beacon. The signal emitted by the beacon may include information indicating the position of the beacon and/or a unique identifier associated with the beacon that may be referenced by the medical device to identify the location of the beacon. It is appreciated that other example beacons may be used. For example, the beacon may include a Radio Frequency Identification (RFID) tag and the medical device may include an RFID reader (e.g., an RFID interrogator) capable of reading the RFID tag to determine the location of the tag and/or the distance between the medical device and the tag. Another example beacon includes WLAN access points. The medical device may identify WLAN access points based on, for example, a Service Set Identification (SSID) label associated with the access point, match the SSID label with an associated location, and determine the distance between the medical device and the WLAN access point based on the received signal strength. A light source may also be employed as a beacon. The light beacon may comprise an illumination device (e.g., an LED) that pulsates at a high frequency consistent with a unique predetermined pattern. The frequency of the light pulsation may be at a sufficiently high frequency to be unperceivable to humans. The medical device may include a light sensing device (e.g., a camera) to detect the light pulses, determine the location of the light beacon based on the pattern of light pulses, and/or determine a distance to the light beacon based on the intensity of the pulses. In addition, other medical devices may be employed as a beacon. For example, a medical device may broadcast a signal once it has determined its location to nearby medical devices. Accordingly, various devices may be employed as beacons for the medical device to use in one or more IPS processes to determine its location.

In at least one example, the IPS processes performed in act 504 include location determination by dead reckoning. Dead reckoning processes may estimate movement relative to a past starting location to determine a present location. The estimated movement may be directly measured by, for example, motion sensors and/or determined based on a previous speed and a previous direction. The starting location may be determined based on one or more IPS and/or GPS methods. For example, the starting location may be a past location determined by GPS and/or a past location determined based on one or more beacons. In addition, the starting location can be provided via input by the patient or other user. Example processes performed by the medical device to perform dead reckoning are described further below with reference to FIGS. 6A-6B.

In act 506, the medical device determines whether GPS information is available. The medical device may determine whether GPS information is available based on one or more predetermined criteria. For example, the medical device may receive GPS signals and determine that GPS information is available by comparing the strength of the GPS signals received and/or the number of satellites associated with the received GPS signals to predetermined thresholds. The threshold number of satellites and/or the threshold signal strength may be stored as configurable parameters and set to minimum levels required to determine the location of the medical device. If the medical device determines that GPS information is available, the medical device proceeds to act 508 and improves the accuracy of the determined location by determining the location based on the GPS information. Example GPS location determination processes are described below with reference to FIGS. 7 and 8.

In some examples, the medical device may include a switch operable by the patient to turn off the GPS capabilities of the medical device. The switch may be a physical switch on the medical device and/or a virtual switch within a user interface of the medical device. According to this example, in the act 506, the medical device may also check the state of the GPS capabilities in the medical device and automatically proceed to act 510 if the GPS capabilities of the medical device are turned off. Otherwise, the medical device may determine whether GPS information is available and proceed as described above. In some examples, the medical device may turn on the GPS capabilities within the medical device irrespective of the state of the switch based on the particular event triggering the process 500. For example, the process 500 may be triggered by a life threatening event and the medical device may make all location determination resources available including, for example, GPS capabilities.

In act 510, the medical device transmits its location to an external system. For example, the medical device may transmit information descriptive of its location to a centralized server via a network interface of the medical device. The medical may also transmit its location to another medical device to expedite a location determination process performed by the other medical device. For example, the known location of the medical device may serve as a known reference point (e.g., as a beacon) used in combination with other beacons by the other medical device to triangulate its location.

Figures 6A, 6B:
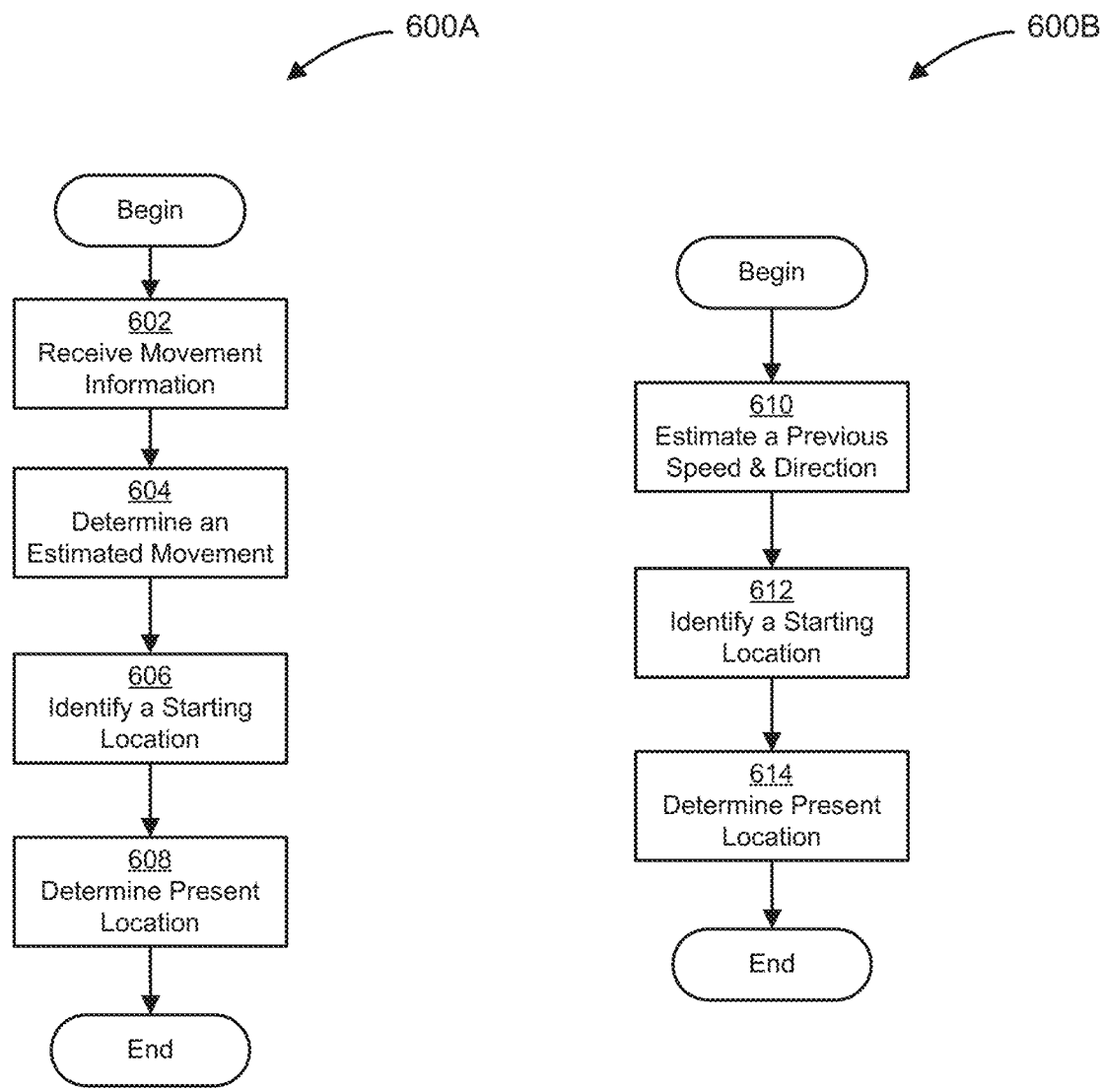
FIGS. 6A-6B are flowcharts of example processes for determining the location of a medical device.

It is appreciated that the particular sequence of steps performed in process 500A may be altered based on the particular implementation. For example, as illustrated by process 500B in FIG. 5B, act 504 of determining the location based on IPS processes may be performed after determining whether GPS information is available in act 506. In process 500B, the IPS processes performed in act 504 may be employed to improve the accuracy of the location determined by GPS in act 508, if GPS signals are available. In addition, the medical device may switch between process 500A and process 500B as the environmental conditions change. Referring to FIG. 6A, an example dead reckoning process 600A executed by, for example, a medical device is illustrated. The dead reckoning process 600A determines the location of the medical device based on motion information from one or more motion detection devices (e.g., magnetometers, accelerometers, and gyroscopes). The dead reckoning process 600A includes the acts of receiving movement information 602, determining an estimated movement 604, identifying a starting location 606, and determining a present location 608.

In act 602, the medical device receives movement information. The movement information may be received from a motion detector device integrated with or communicatively coupled to the medical device. The motion information may include acceleration information, rotational information, and/or heading information.

In act 604, the medical device determines an estimated movement. The medical device may determine the estimated movement based on the movement information received from the motion detector. The medical device may determine the estimated movement by determining an estimated velocity and an associated direction over a period of time. For example, the medical device may determine a directional vector having a magnitude representative of the distance traveled over the period of time and a direction traveled relative to a starting location.

In act 606, the medical device identifies a starting location. The starting location may be stored in, for example, data storage of the medical device. The starting location may be the last computed location of the medical device. It is appreciated that the starting location may be previously determined by other location determination methods including, for example, various GPS methods as described below with reference to FIGS. 7 and 8, previous iterations of the dead reckoning process 600, and/or other IPS processes.

In act 608, the medical device determines its present location based on the estimated movement and the starting location. As previously described, the estimated movement may be represented by a vector indicating the direction traveled and distance traveled by the medical device relative to a starting location. The medical device may add the vector representative of the movement of the medical device to the starting location identified in act 606. The medical device may employ map information stored, for example, in memory to determine a street address of the current location of the medical device and/or identify a particular room within a building where the medical device is located. It is appreciated that the medical device may store the estimated present location in data storage to be employed in act 606 of future iterations of the dead reckoning process 600A.

In some examples, the dead reckoning processes may estimate the movement of the medical device relative to a starting position based on a previous speed and direction of the medical device (e.g., a previous velocity of the medical device). Such an example dead reckoning process is illustrated by dead reckoning process 600B in FIG. 6B. The dead reckoning process 600B includes the acts of estimating a previous speed and direction 610, identifying a starting location 612, and determining a present location 614.

In act 610, the medical device estimates a previous speed and direction of the medical device. The previous speed of the medical device may be determined by identifying a distance between two previous locations of the medical device and an amount of time taken to traverse the distance. For example, the medical device may determine that a distance of fifteen meters was traversed by the medical device in ten seconds. In this example, the medical device may divide the distance traveled by the amount of time taken to travel the distance to yield a resulting estimated speed of 1.5 meters per second. The previous direction of travel may be determined in a similar way based on previous known locations. For example, the medical device may generate a unity vector indicative of the direction of travel of the medical device based on two previous locations.

It is appreciated that, in some examples, motion information from a motion sensor may be employed to supplement the estimated previous speed and direction computation described above or vice-versa. For example, the medical device may estimate the speed and direction of travel during periods of time where motion information is unavailable as a gap-filler.

In act 612, the medical device identifies a starting location. The starting location may be, for example, the most recently determined location of the medical device. The previous location identified as the starting location and/or the previous locations employed in act 610 may be previously determined by other location determination methods including, for example, various GPS methods as described below with reference to FIGS. 7 and 8, previous iterations of the dead reckoning processes 600A-B, and/or other IPS processes.

In act 614, the medical device determines its present location based on the previous speed, the previous direction, and the starting location. For example, the medical device may identify an amount of time that has elapsed since the medical device was at the starting location and multiply that identified amount of time by the previous speed to determine an estimated distance traveled. In one example, the medical device may identify that twenty seconds has elapsed and the speed of travel was 1.5 meters per second yielding a result of thirty meters traveled. The medical device may combine the distance traveled with the previous direction to generate a vector indicative of the distance traveled and the direction of the distance traveled. The generated vector may be added to the starting location to identify a present location of the medical device. The medical device may store the estimated present location in data storage to be employed in future iterations of the dead reckoning process 600B.

It is appreciated that the medical device may employ map information stored, for example, in memory to determine a street address of the current location of the medical device and/or identify a particular room within a building where the medical device is located. The map information may also be employed to improve the accuracy of the resulting present location. For example, the dead reckoning processes 600A and/or 600B may yield a resulting coordinate that is unlikely for the medical device to be positioned (e.g., in a wall between two rooms). In this example, the medical device may adjust the final location of the medical device to a nearby position that is more likely (e.g., in one of the two rooms separated by the wall).

Figure 7:
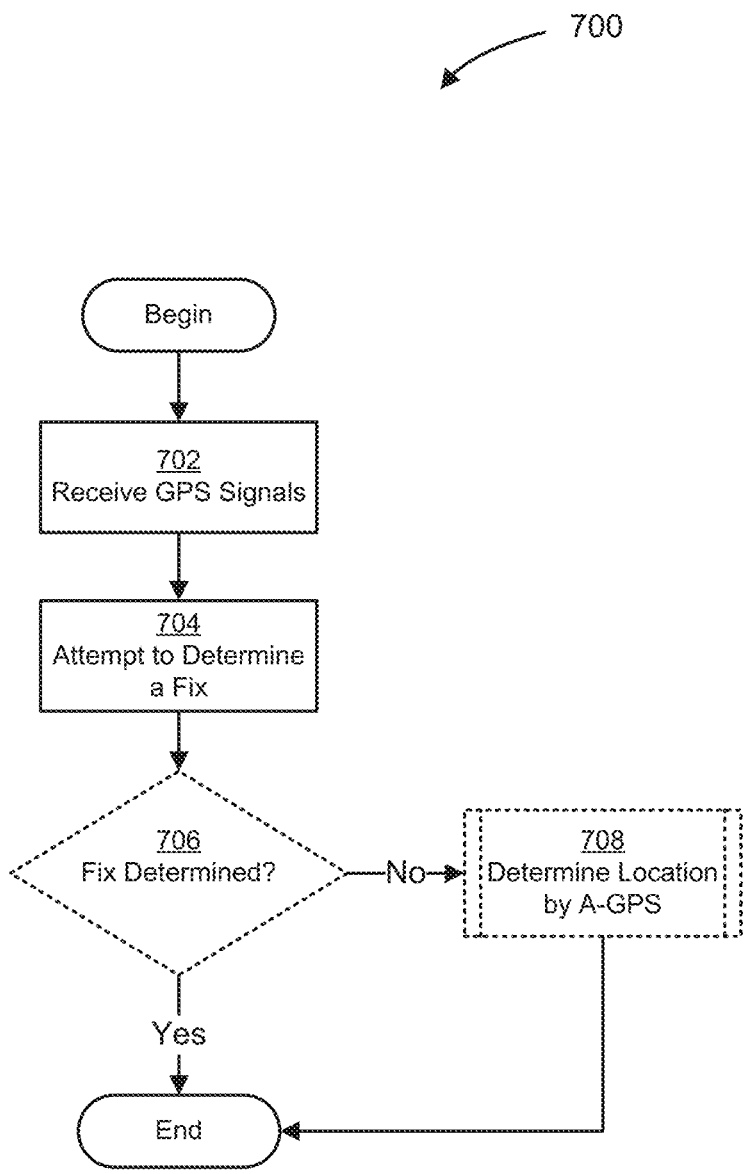
FIG. 7 is a flowchart of another example process for determining the location of a medical device.

Referring to FIG. 7, an example location determination process 700 employed by, for example, a medical device is illustrated. The location determination process 700 determines the location of the medical device based on available GPS signals. It is appreciated that any GPS location determination technique or combination of techniques may be employed in process 700 including, for example, high sensitivity GPS, DGPS, WAAS, or Defense Advanced GPS.

Referring back to FIG. 7, the location determination process 700 includes the acts of receiving GPS information 702 and attempting to determine a fix 704. In some examples, the location determination process 700 may switch to an A-GPS process if a fix is not determined in act 704. A-GPS methods leverage the cellular network to facilitate the determination of a fix. In these examples, the Location determination process 700 also includes acts of determining whether the fix was determined 706 and determining the location by A-GPS 708.

In act 702, the medical device and/or a GPS receiver in communication with the medical device receives GPS information. The GPS information may be received by one or more antennas coupled to a network interface and/or a sensor interface of the medical device.

In act 704, the medical device and/or a GPS receiver in communication with the medical device attempts to determine a fix based on the GPS information. The fix may be determined by triangulating the location of the medical device relative to a plurality of GPS satellites based on the received GPS information. The medical device may employ map information stored, for example, in memory to determine a street address associated with the GPS determined location (e.g., GPS coordinates) of the medical device and/or identify a particular room within a building where the medical device is located. It is appreciated that the particular method employed to determine the fix and the accuracy of the resulting location determination may vary based on the type of GPS selected. In high sensitivity GPS systems, for example, the received GPS signal is integrated for up to 1,000 times longer than in conventional GPS systems and, thereby, can determine a fix with GPS signals 30 decibels (db) weaker than conventional systems (e.g., in indoor environments). In DGPS receivers, the receiver receives GPS signals from GPS satellites and GPS error information broadcast by a network of fixed, ground stations. The ground stations determine GPS error information by comparing the fix determined based on the GPS signals with the actual location of the ground station. The determined GPS error at a nearby tower is likely close to the same error encountered by a nearby medical device. Accordingly, DGPS offers improved accuracy relative to conventional GPS systems. WAAS receivers, similar to DGPS receivers, receive both GPS signals and GPS error information to determine location. WAAS receivers, however, receive the GPS error information from satellites rather than from ground stations.

Other receivers may employ still yet other methods to receive GPS information and determine a fix. Some GPS methods, like defense advanced GPS receivers, may require additional steps such as decoding encrypted GPS signals.

As discussed above in some examples, the process 700 includes the additional acts 706 and 708 to switch to an A-GPS process if a fix is not determined. In the optional act 706, the medical device determines whether a fix was determined in the act 704. The medical device may wait a threshold period of time and/or have a threshold number of failed location requests from, for example, the processor to a GPS receiver. For example, the medical device may attempt to determine a fix within the predetermined constraints. If the medical device does not determine a fix within the predetermined constraints, the medical device may proceed to optional act 708 and determine the location of the medical device by A-GPS. Example processes employed by the medical device to determine its location by A-GPS are described with reference to FIG. 8 below. Otherwise, the medical device determines its location based on GPS and ends process 700. If optional acts 706 and 708 are not performed, the medical device may proceed to determine a fix based on the GPS information in act 704.

A-GPS processes described herein reduce the time required for a GPS location system to determine a fix by, for example, providing an estimated location to the GPS location system and/or providing GPS satellite information to the GPS location system that would otherwise have to be downloaded from satellites at a slow rate. FIG. 8 illustrates an example A-GPS process including the acts of receiving GPS information 802, acquiring satellite information 804, and determining a fix based on the GPS information and the satellite information 806.

In act 802, the medical device receives GPS information. The GPS information may be received by one or more antennas coupled to a network interface of the medical device.

In act 804, the medical device acquires GPS satellite information from a network connection. The satellite information includes ephemeris data (e.g., information regarding the position of the satellite in the orbit) and/or almanac data (e.g., information regarding the time and status of the entire satellite constellation). The medical device may acquire the satellite information from a communication link to a server via, for example, a cellular network tower.

In act 806, the medical device determines the location of the medical device based on the GPS information and the GPS satellite information. For example, the medical device may determine the range between the medical device and the various satellites based on the GPS information and determine the location of the satellites in the orbit based on the satellite information. The medical device may determine its location by triangulation based on the determined location of the GPS satellites and their respective ranges.

Each of the processes disclosed herein depicts one particular sequence of acts in a particular example. The acts included in each of these processes may be performed by, or using, a medical device specially configured as discussed herein. Some acts are optional and, as such, may be omitted in accord with one or more examples. Additionally, the order of acts can be altered, or other acts can be added, without departing from the scope of the systems and methods discussed herein. In addition, as discussed above, in at least one example, the acts are performed on a particular, specially configured machine, namely a medical device configured according to the examples disclosed herein. Additional example medical device location determination processes are described in the '368 application.

The medical device location determination processes have a variety of potential applications. The medical device location determination processes may be employed, for example, to assist medical personnel locate a patient in need of medical attention and/or administer physical activity tests to the patient to gather additional information regarding the medical condition of the patient.

Example Physical Activity Tests

Various examples implement a variety of systems and processes in a medical device to facilitate the treatment of the patient by enabling the medical device to determine its location. A wearable medical device (e.g., wearable medical device 100, a cardiac monitoring device, etc.) capable of determining its location may be employed to administer physical activity tests to gather patient data under controlled conditions including, for example, the distance traveled during the physical activity. In these examples, the wearable medical device may guide or prompt the patient throughout the physical activity test, while protecting the patient from, for example, cardiac arrest by providing external defibrillation capabilities as appropriate. Various sensors within the wearable medical device may monitor physiological parameters of the patient including, for example, the heart rate, blood oxygen saturation, and recovery time before, during, and after the physical activity to a baseline heart rate. These physical activity tests may include, for example, a six minute walk test as described in U.S. Pat. No. 8,140,154, titled "WEARABLE MEDICAL TREATMENT DEVICE," issued on Mar. 20, 2012, which is hereby incorporated herein by reference herein in its entirety, and the paper "Guidelines for the Six-Minute Walk Test" published by the American Thoracic Society in March 2002, which is hereby incorporated herein by reference herein in its entirety.

Figure 9:
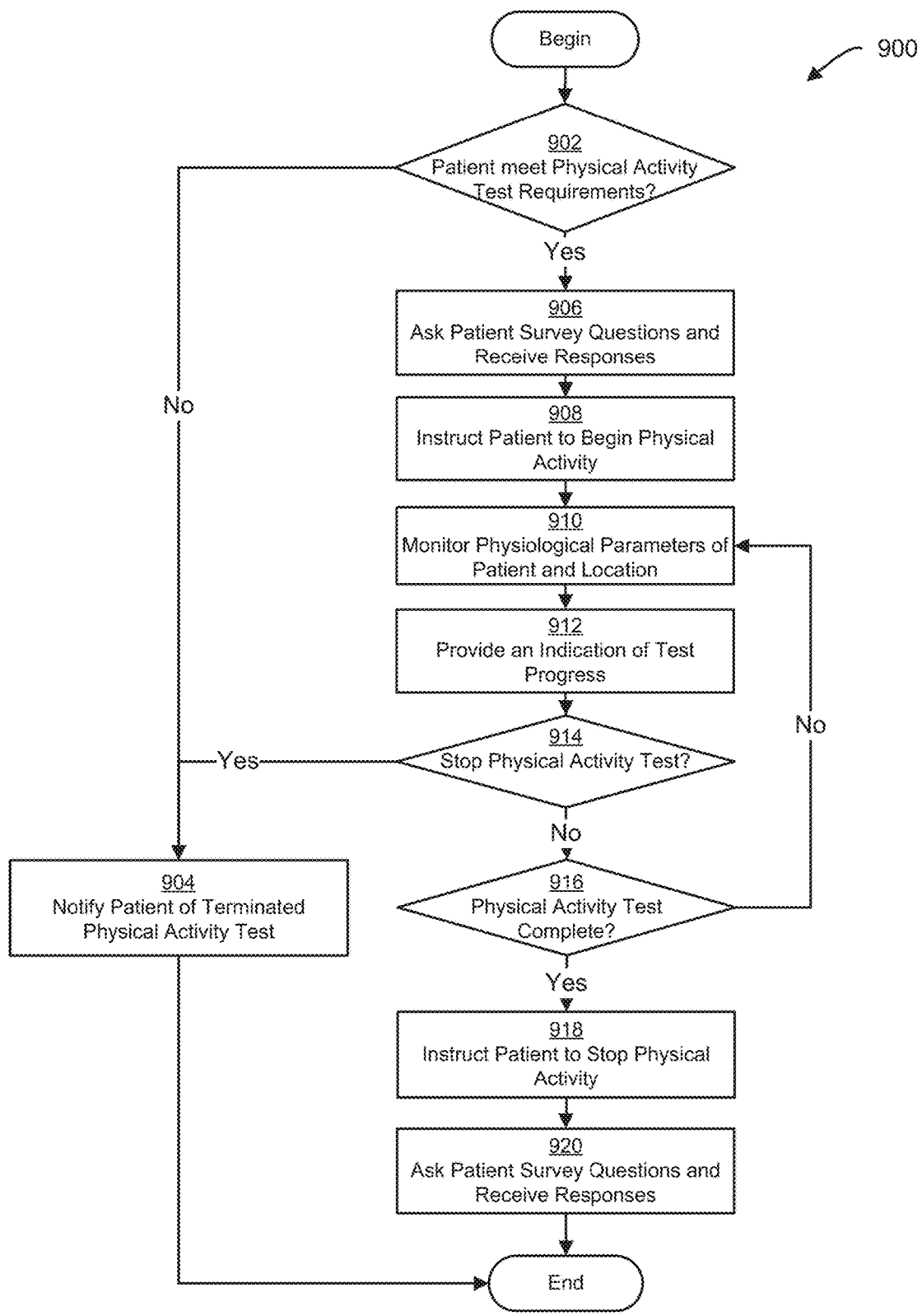
FIG. 9 is a flowchart of an example process for administering a physical activity test.

FIG. 9 illustrates an example physical activity test process 900 executed by a medical device. The physical activity test process 900 includes the acts of determining whether a medical condition is detected 902, notifying the patient of the medical condition 904, asking patient survey questions and receiving responses 906, instructing the patient to begin physical activity 908, monitoring the medical condition and location of the patient 910, providing an indication of the test progress 912, determining whether a medical condition is detected 914, determining whether the physical activity test is complete 916, instructing the patient to stop physical activity 918, and asking patient survey questions and receiving responses 920.

In act 902, the medical device determines whether the patient meets the requirements associated with the physical activity test. In some examples, the medical device may require that the patient is not currently experiencing a heart related condition (e.g., an arrhythmia, ventricular fibrillation, atrial fibrillation, pulseless electrical activity, or asystole). In addition, the medical device may have a minimum time interval requirement between administration of physical activity tests. For example, the medical device may require that the patient has not previously performed the physical activity test within the past ten hours. If the medical device determines that the patient meets the requirements of the physical activity test, the medical device proceeds to act 906 and asks the patient survey questions and receives responses. Otherwise, the medical device proceeds to act 904 and notifies the patient of the termination of the physical activity test.

In act 906, the medical device asks the patient survey questions and receives responses. The medical device may ask the survey questions to the patient by a speaker of the medical device and/or display the questions on a display screen of the medical device. The survey questions may include, for example, "what's your shortness of breath level?" and/or "what's your fatigue level?" The medical device may receive responses in various forms. In some examples, the medical device includes voice-recognition capabilities and records the patient's answer as text. In other examples, the medical device may present a touch-screen interface via a display of the medical device to the patient including a sliding scale. For example, the user may select zero in response to the question "what's your fatigue level?" to indicate that they are not tired at all and may select 10 to indicate that they are very tired.

In act 908, the medical device instructs the patient to begin the physical activity. The instructions may be visual instructions presented to the user via a display of the medical device and/or audible instructions played via a speaker of the medical device. It is appreciated that the particular instructions to the patient may vary based on the physical activity employed in the physical activity test. In one example, the physical activity is a six minute walk test and the medical device instructs the patient to begin walking. The instructions may further include specific directions and/or guidance. For example, the medical device may instruct the patient to walk on level ground during the six minute walk test.

In act 910, the medical device monitors physiological parameters associated with the patient and the location of the medical device. The medical device may monitor its location by performing, for example, various location determination processes as previously described with reference to FIGS. 5-8. In one example, the medical device automatically performs the dead reckoning location determination process illustrated in FIG. 6A in act 910. Employing the dead reckoning location determination process during the physical activity test to track location may be advantageous because the patient is likely indoors where GPS signals are generally weak. The medical device may also monitor various physiological parameters including for example heart rate, ECG, blood oxygen saturation, and gait.

In act 912, the medical device provides an indication of the patient's progress in the physical activity test. For example, the medical device may display a status bar via a display of the medical device indicating how much time is remaining in the physical activity test. The medical device may also issue audible alerts to the patient indicating the patient's progress via a speaker of the medical device.

In act 914, the medical device determines whether to stop the physical activity test. The medical device may be configured to stop the physical activity test based on a variety of parameters. In some examples, the medical device stops the physical activity test responsive to identifying a heart condition in the data gathered in act 910. For example, the ECG signal of the patient may indicate that the patient is experiencing an arrhythmia and the medical device may stop the physical activity test in act 914. The medical device may also be configured to receive stop requests from the patient. For example, the medical device may present a button to the user via a display to stop the physical activity test because, for example, the patient is feeling lightheaded. If the medical device stops the physical activity test, the medical device proceeds to act 904 and notifies the patient of the termination of the physical activity test. Otherwise, the medical device proceeds to act 916 and determines whether the physical activity test is complete.

In act 916, the medical device determines whether the physical activity test is complete. It is appreciated that the specific criteria employed to determine that the physical activity test is complete may vary based on the particular activity performed during the test. In one example, the physical activity test is a six minute walk test and the medical device determines that the physical activity test is complete after six minutes has passed. If the medical device determines that the physical activity test is complete, the medical device proceeds to act 918 and instructs the patient to stop the physical activity. Otherwise the medical device returns to act 910 and continues to monitor the physiological parameters of the patient and the location of the medical device.

In act 918, the medical device instructs the patient to stop the physical activity. The instructions may be visual instructions presented to the user via a display of the medical device and/or audible instructions played via a speaker of the medical device. It is appreciated that the particular instructions to the patient may vary based on the physical activity employed in the physical activity test. In one example, the physical activity is a six minute walk test and the medical device instructs the patient to stop walking.

In act 920, medical device asked the patient survey questions and receives responses. The survey questions employed in act 920 may be similar to the survey questions asked at the beginning of the physical activity test in act 906. Similarly, the medical device may include voice recognition capabilities and store the patient's response as text and/or present a user interface to the patient to receive a response.

In some examples, a medical device generates a patient report based on the patient information gathered during the physical activity test. The patient report may include the various monitor health parameters associated with the patient during the physical activity test and the distance traveled during the test (e.g., measured by the location determination processes described above). The report may also include information regarding the gait of the patient during the physical activity test and/or information regarding the likelihood of the patient getting Alzheimer's disease or other forms of dementia. The report may further include an omnibus quality of life score based on sensed conditions. This aggregate score can be compared with a threshold value to indicate whether or when the patient requires treatment. It is appreciated that the generated report may be transmitted to a remote computing device associated with a physician.

Example Maps

Figure 10:
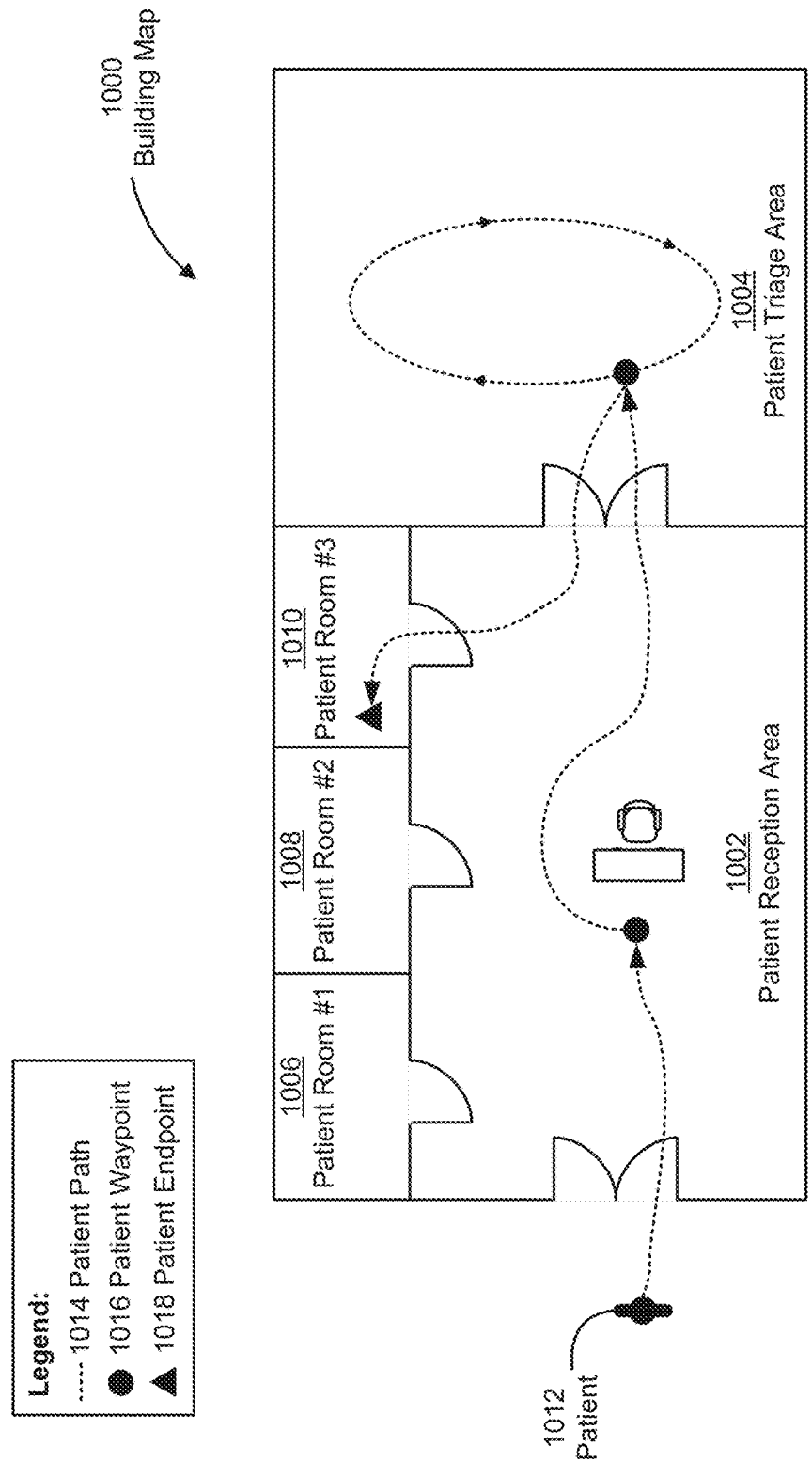
FIG. 10 is an illustration of an example building map.

In some examples, the medical device stores map information descriptive of various maps (e.g., building maps and street maps) to facilitate patient tracking. For example, the medical device may determine the location of the patient by employing one or more of the processes described above. The medical device may cross-reference a determined GPS coordinate and altitude with the determined location to identify a specific room within a building (e.g., in a patient triage area of a particular hospital). In addition, the map information may be employed to improve the accuracy of a determined location. For example, the medical device may determine that the patient is within a ten meter radius of a particular location within a building having an increasing altitude. The medical device may identify a staircase within the identified ten meter radius based on map information and determine that the patient is on the staircase climbing the stairs. An example building map 1000 for a hospital is illustrated in FIG. 10. The building map 1000 includes a patient reception area 1002, a patient triage area 1004, a first patient room 1006, a second patient room 1008, and a third patient room 1010. The tracked movement of a patient 1012 wearing, for example, an ambulatory medical device is overlaid onto the building map 1000 as illustrated by the patient path 1014, the patient waypoints 1016, and the patient endpoint 1018.

As illustrated in FIG. 10, the medical device tracks patient location as the patient 1012 moves from outside the building to the waypoint 1016 in the patient reception area 1002 via the patient path 1014. In some examples, the medical device may determine the location of the patient 1012 at the entrance to the building based on one or more available location information sources (e.g., by processes 700 and/or 800 illustrated in FIGS. 7 and 8).

Once in the building, the medical device can employ one or more IPS methods to track the patient movement within the building as described above. For example, the location of the patient at the entrance to the building may be employed as the initial starting location for IPS and dead reckoning processes.

For example, the medical device may employ radio waves, magnetic fields, acoustic signals (e.g., ultrasonic device localization), or other sensory information collected by, e.g., mobile devices, to assist in locating a position of the patient. For example, the medical device can rely on distance measurement to nearby "anchor" nodes, e.g., nodes with known positions, such as WiFi access points. In some examples, magnetic positioning can be used based on magnetic sensor data from, e.g., personal digital devices such as smartphones, to wirelessly locate the patient inside the building. In some implementations, the magnetic positioning information can be optimized using, for example, WiFi and Bluetooth location information. An example of magnetic positioning technologies as described herein is provided by IndoorAtlas Inc. of Mountain View Calif. For example, magnetic positioning can offer an indoor accuracy of, e.g., 1-2 meters with between 90-95% confidence level, without using additional wireless infrastructure for positioning.

Other example IPS methods include tracking location by analyzing the received signal strength of wireless signals received from Bluetooth® beacons, light beacons, WLAN access points, and/or RFID tags as described above.

As the patient 1012 proceeds through the patient reception area 1002 to the patient triage area 1004, the medical device may continue to monitor the location of the patient 1012. In some examples, the medical device may track the location of the patient as the patient performs one or more physical activity tests. As illustrated, the patient travels in an elliptical path within the patient triage area 1004 to perform a physical activity test (e.g., a six-minute walk test). The medical device may determine, for example, the distance traveled by the patient 1012 during the physical activity test and may report the distance traveled to an external system associated with the hospital. The medical device may further track the location of the patient as the patient proceeds from the patient triage area 1004 to the third patient room 1010 and farther to patient endpoint 1018.

In some examples, the medical device provides an indication of the path of the patient to an external entity via one or more display mechanisms (e.g., a display screen). For example, the medical device may display a building map with an overlaid patient path as illustrated in FIG. 10. It is appreciated that the particular visual representation employed to display the path of the patient may vary. For example, the location of the patient may be represented by a picture of the patient (or some other indicator of patient identity) that moves along the patient path on the map. In addition, the medical device may also provide information regarding the path of a patient to an external entity. For example, a patient may experience a cardiac event (e.g., ventricular fibrillation) and the medical device may provide building and/or street maps with overlaid patient paths to a physician associated with the patient to analyze what activities the patient performed just prior to the cardiac event.

Having thus described several aspects of at least one example of this disclosure, it is to be appreciated various alterations, modifications, and improvements will readily occur to those skilled in the art. Such alterations, modifications, and improvements are intended to be part of this disclosure, and are intended to be within the scope of the disclosure. Accordingly, the foregoing description and drawings are by way of example only.

What is claimed is:

1. A wearable medical device comprising:
a plurality of sensing electrodes to sense an electrocardiogram signal of a patient;
a plurality of therapy electrodes to provide treatment to the patient;
a garment to be worn about a torso of the patient and receive the plurality of sensing electrodes and the plurality of therapy electrodes;
a motion detector;
a processor coupled to the plurality of sensing electrodes, the plurality of therapy electrodes, and the motion detector; and
a memory communicatively coupled to the processor and comprising instructions that when executed by the processor cause the processor to:
receive movement information comprising at least acceleration information and heading information from the motion detector;
detect a movement of the wearable medical device from the movement information received from the motion detector, wherein the movement of the wearable medical device comprises a distance traveled by the wearable medical device and a direction traveled by the wearable medical device; and
estimate a current location of the wearable medical device relative to a previous location of the wearable medical device using dead reckoning based at least in part on the distance traveled by the wearable medical device and the direction traveled by the wearable medical device.

2. The wearable medical device of claim 1, wherein the motion detector includes a gyroscope, an accelerometer, or a magnetometer.

3. The wearable medical device of claim 1, comprising an antenna coupled to the processor and wherein the instructions cause the processor to transmit, via the antenna, the location of the wearable medical device to an external system.

4. The wearable medical device of claim 1, wherein the instructions cause the processor to track the location of the wearable medical device at least in part by identifying a starting location of the wearable medical device, determining an estimated movement of the wearable medical device based on the detected movement of the wearable medical device, and determining the location of the wearable medical device based on the starting location and the estimated movement.

5. The wearable medical device of claim 1, wherein the instructions cause the processor to administer a physical activity test to the patient and measure a distance traveled by the patient during the physical activity test.

6. The wearable medical device of claim 5, wherein the instructions cause the processor to monitor a gait of the patient during the physical activity test and determine a likelihood of the patient developing a form of dementia based on the gait of the patient.

7. The wearable medical device of claim 5, wherein the physical activity test includes a six minute walk test.

8. The wearable medical device of claim 5, comprising an antenna coupled to the processor and wherein the instructions cause the processor to generate a patient report based on the administered physical activity test and transmit, via the antenna, the patient report to an external system.

9. The wearable medical device of claim 1, comprising a memory coupled to the processor to store building map information and wherein the instructions cause the processor to track the location of the wearable medical device within a building based on the detected movement of the wearable medical device and the building map information.

10. The wearable medical device of claim 1, comprising an antenna coupled to the processor to receive location information.

11. The wearable medical device of claim 10, wherein the instructions cause the processor to determine whether the location information is available from the antenna, determine the location of the wearable medical device based on the location information responsive to the location information being available, and determine the location of the wearable medical device based on the detected movement of the wearable medical device responsive to the location information being unavailable.

12. The wearable medical device of claim 10, comprising a switch to control a capability of the wearable medical device to receive the location information from the antenna and wherein the instructions cause the processor to determine, based on a state of the switch, the location of the wearable medical device from one of: the detected movement of the wearable medical device and the location information.

13. The wearable medical device of claim 10, wherein the instructions cause the processor to attempt to determine the location of the wearable medical device based on the location information within a predetermined period of time and determine the location of the wearable medical device based on the detected movement of the wearable medical device responsive to failing to determine the location of the wearable medical device based on the location information within the predetermined period of time.

14. The wearable medical device of claim 10, wherein the location information includes a signal from a global positioning system, a BLUETOOTH beacon, a WLAN access point, or a radio frequency identification tag.

15. The wearable medical device of claim 1, wherein the processor is configured to estimate the current location of the wearable medical device relative to the previous location of the wearable medical device using dead reckoning in response to at least one of detecting a loss of consciousness of the patient and detecting that the patient has fallen.

16. A wearable medical device comprising:
a plurality of sensing electrodes to sense an electrocardiogram signal of a patient;
a plurality of therapy electrodes to provide treatment to the patient;
a garment to be worn about a torso of the patient and receive the plurality of sensing electrodes and the plurality of therapy electrodes; and
a processor operatively coupled to the plurality of sensing electrodes and the plurality of therapy electrodes; and
a memory communicatively coupled to the processor and comprising instructions that when executed by the processor cause the processor to:
detect a movement of the wearable device comprising a speed of the wearable medical device and a direction of movement of the wearable medical device; and
estimate a current location of the wearable medical device by dead reckoning relative to a previous location of the wearable medical device based at least in part on the speed of the wearable medical device and the direction of movement of the wearable medical device.

17. The wearable medical device of claim 16, wherein the instructions cause the processor to identify an elapsed time since the wearable medical device was at the previous location.

18. The wearable medical device of claim 17, wherein the instructions cause the processor to identify a distance traveled by the wearable medical device based on the elapsed time and a previous speed of the wearable medical device.

19. The wearable medical device of claim 18, wherein the instructions cause the processor to identify the current location based on the distance traveled by the wearable medical device and the previous location.

20. The wearable medical device of claim 16, comprising a motion detector coupled to the processor and wherein the instructions cause the processor to identify the previous speed of the wearable medical device based on detected motion of the wearable medical device.

21. The wearable medical device of claim 16, wherein the processor is configured to estimate the current location of the wearable medical device by dead reckoning relative to a previous location of the wearable medical device in response to at least one of detecting a loss of consciousness of the patient and detecting that the patient has fallen.

22. An ambulatory medical device comprising:
a plurality of sensing electrodes to sense an electrocardiogram signal of a patient;
a memory to store building map information including a layout of a building; and
a processor coupled to the plurality of sensing electrodes and the memory;
wherein the memory comprises instructions that when executed by the processor cause the processor to:
monitor cardiac events of the patient,
detect a movement of the ambulatory medical device comprising at least acceleration information and heading information;
estimate a current location of the ambulatory medical device within the building using dead reckoning based at least in part on the acceleration information and the heading information; and
generate a building map with a location history of the ambulatory medical device based on the building map information and the estimated current location of the ambulatory medical device.

23. The ambulatory medical device of claim 22, comprising a display coupled to the processor and wherein the instructions cause the processor to display, via the display, the building map with the location history of the ambulatory medical device.

24. The ambulatory medical device of claim 22, comprising an antenna coupled to the processor and wherein the instructions cause the processor to transmit, via the antenna, the building map with the location history of the ambulatory medical device to an external system.

25. The ambulatory medical device of claim 22, wherein the instructions cause the processor to administer a physical activity test to the patient and track the location of the ambulatory medical device during the physical activity test.

26. The ambulatory medical device of claim 25, wherein the physical activity test includes a six minute walk test.

27. The ambulatory medical device of claim 25, wherein the instructions cause the processor to generate a patient report based on the administered physical activity test including a building map with a location history of the ambulatory medical device during the physical activity test.

28. The ambulatory medical device of claim 27, comprising an antenna coupled to the processor and wherein the instructions cause the processor to transmit, via the antenna, the patient report to an external system.

29. The ambulatory medical device of claim 22, wherein the ambulatory medical device is one of: a wearable defibrillator, an in-hospital defibrillator, and a mobile cardiac telemetry monitor.

30. The ambulatory medical device of claim 22, further comprising:
 a motion detector;
 wherein the instructions cause the processor to detect, using the motion detector, a movement of the ambulatory medical device, wherein the instructions further cause the processor to
 estimate the current location of the ambulatory medical device at least in part by identifying a starting location of the ambulatory medical device in the building, determining an estimated movement of the ambulatory medical device based on the detected movement of the ambulatory medical device from movement information received from the motion detector, and determining the tracked location of the ambulatory medical device based on the starting location and the estimated movement.

31. The ambulatory medical device of claim 22, further comprising:
 an antenna coupled to the processor to receive location information; and
 a motion detector;
 wherein the instructions cause the processor to detect a movement of the ambulatory medical device, wherein the instructions further cause the processor to determine whether the location information is available from the antenna, determine the tracked location of the ambulatory medical device based on the location information responsive to the location information being available, and estimate the current location of the ambulatory medical device based on the detected movement of the ambulatory medical device responsive to the location information being unavailable.

32. The ambulatory medical device of claim 22, wherein the instructions cause the processor to identify an elapsed time since the ambulatory medical device was at a previous location.

33. The ambulatory medical device of claim 32, wherein the instructions cause the processor to identify a distance traveled by the ambulatory medical device based on the elapsed time and a previous speed of the ambulatory medical device.

34. The ambulatory medical device of claim 33, wherein the instructions cause the processor to determine the tracked location based on the distance traveled by the ambulatory medical device and the previous location.

35. The ambulatory medical device of claim 22, further comprising a motion detector coupled to the processor, and wherein the instructions cause the processor to identify a previous speed of the ambulatory medical device based on detected motion of the ambulatory medical device.

36. The ambulatory medical device of claim 22, wherein the processor is configured to estimate the current location of the ambulatory medical device within the building using dead reckoning in response to at least one of detecting a loss of consciousness of the patient and detecting that the patient has fallen.

\* \* \* \* \*